(12) United States Patent
Shoshan-Barmatz et al.

(10) Patent No.: US 8,440,788 B2
(45) Date of Patent: May 14, 2013

(54) N-TERMINAL VDAC VARIANTS AND USES THEREOF

(75) Inventors: Varda Shoshan-Barmatz, Omer (IL); Doron Calo, Petah Tikva (IL)

(73) Assignee: Ben-Gurion University of The Negev Research and Development Authority Ltd., Beer Sheva (IL)

( * ) Notice: Subject to any disclaimer, the term of this patent is extended or adjusted under 35 U.S.C. 154(b) by 1000 days.

(21) Appl. No.: 12/296,239

(22) PCT Filed: Apr. 10, 2007

(86) PCT No.: PCT/IL2007/000455
§ 371 (c)(1),
(2), (4) Date: Feb. 3, 2009

(87) PCT Pub. No.: WO2007/113837
PCT Pub. Date: Oct. 11, 2007

(65) Prior Publication Data
US 2010/0075898 A1 Mar. 25, 2010

Related U.S. Application Data

(60) Provisional application No. 60/789,570, filed on Apr. 6, 2006.

(51) Int. Cl.
*C07K 14/00* (2006.01)
*A61K 38/00* (2006.01)
*A61K 48/00* (2006.01)
*A61P 43/00* (2006.01)
*C07H 21/04* (2006.01)
*C12N 15/63* (2006.01)
*C12N 15/85* (2006.01)

(52) U.S. Cl.
USPC ......... 530/300; 530/402; 514/17.4; 514/18.9; 514/44; 536/23.1; 536/23.5; 435/320.1; 435/325

(58) Field of Classification Search .................. None
See application file for complete search history.

(56) References Cited

U.S. PATENT DOCUMENTS

| | | | |
|---|---|---|---|
| 5,288,707 A | 2/1994 | Metternich | |
| 5,391,377 A | 2/1995 | Barnwell | |
| 5,550,251 A | 8/1996 | Hirschmann | |
| 5,552,534 A | 9/1996 | Hirschmann | |
| 5,780,235 A | 7/1998 | Bandman | |
| 5,811,392 A | 9/1998 | Gilon | |
| 5,910,478 A | 6/1999 | Hlavka | |
| 5,965,539 A | 10/1999 | Sebti | |
| 6,291,247 B1 | 9/2001 | Riopelle | |
| 7,276,588 B2 * | 10/2007 | Pizzo et al. | 530/388.2 |
| 2005/0234116 A1 | 10/2005 | Sugiyama | |
| 2006/0252822 A1 | 11/2006 | Cesura | |

FOREIGN PATENT DOCUMENTS

| | | |
|---|---|---|
| EP | 1491194 | 12/2004 |
| WO | 02/12340 | 2/2002 |
| WO | 03/087768 | 10/2003 |
| WO | 2005/007878 | 1/2005 |
| WO | 2006/095347 | 9/2006 |

OTHER PUBLICATIONS

Mammalian Gene Collection (Francis Collins), 2002, Generation and initial analysis of more than 15,000 full-length human and mouse cDNA sequences. PNAS, 99(26): 16899-16903, esp. Accession No. BC060558.1.*
Abu-Hamad S et al., "The expression level of the voltage-dependent anion channel controls life and death of the cell", Proc Natl Acad Sci U S A. Apr. 11, 2006;103(15):5787-5792 (2006).
Arselin et al., "The GxxxG motif of the transmembrane domain of subunit e is involved in the dimerization/oligomerization of the yeast ATP synthase complex in the mitochondrial membrane", Eur. J. Biochem. 270:1875-1884 (2003).
Azoulay-Zohar et al., "In self-defence: hexokinase promotes voltage-dependent anion channel closure and prevents mitochondria-mediated apoptotic cell death", Biochemical J., 377(Pt 2):347-355 (2004).
Babel D. et al., "Studies on human porin. VI. Production and characterization of eight monoclonal mouse antibodies against the human VDAC"Porin 31HL" and their application for histotopological studies in human skeletal muscle", Biol. Chem. Hoppe. Seyler., 372:1027-1034 (1991).
Bae et al., "Ruthenium red, inhibitor of mitochondrial Ca2+ uniporter, inhibits curcumin-induced apoptosis via the prevention of intracellular Ca2+ depletion and cytochrome c release", Biochem. Biophys. Res. Commun., 303(4):1073-1079 (2003).
Colombini M., "VDAC: the channel at the interface between mitochondria and the cytosol", Mol. Cell Biochem., 256-257(1-2):107-115 (2004).
De Pinto et al., "New functions of an old protein: the eukaryotic porin or voltage dependent anion selective channel (VDAC)", Ital. J. Biochem., 52(1):17-24 (2003).
Doran and Halestrap, "Cytochrome c release from isolated rat liver mitochondria can occur independently of outer-membrane rupture: possible role of contact sites", Biochem. J., 348(Pt. 2): 343-350 (2000).
Gincel et al., "Calcium binding and translocation by the voltage-dependent anion channel: a possible regulatory mechanism in mitochondrial function", Biochem. J., 358 (Pt. 1):147-155 (2001).
Koppel et al., "Bacterial expression and characterization of the mitochondrial outer membrane channel. Effects of n-terminal modifications", J. Biol. Chem., 273(22):13794-13800 (1998).
Koumenis C. et al., "Identification of three proteins in the eye of Aplysia, whose synthesis is altered by serotonin (5-HT). Possible involvement of these proteins in the ocular circadian system", J. Biol. Chem. 270(4):14619-14627 (1995).
Krause et al., "Cross-linking analysis of yeast mitochondrial outer membrane", Biochim. Biophys. Acta., 860(3):690-698 (1986).

(Continued)

*Primary Examiner* — Joanne Hama
*Assistant Examiner* — Sandra Wegert
(74) *Attorney, Agent, or Firm* — Rodney J. Fuller; Booth Udall Fuller, PLC

(57) ABSTRACT

The present invention relates generally to variants and peptides of the mitochondrial protein, voltage-dependent anion channel (VDAC) and to polynucleotides encoding same. In particular, the present invention is directed to N-terminal truncated and mutated VDAC and specific amino acid and polynucleotide sequences thereof useful in inhibiting apoptosis, and to pharmaceutical compositions comprising same useful in the treatment of diseases associated with excess apoptosis.

14 Claims, 10 Drawing Sheets

OTHER PUBLICATIONS

Kroemer et al., "Mitochondrial control of apoptosis", Immunol. Today, 18(1):44-51 (1997).

Malia and Wagner, "NMR structural investigation of the mitochondrial outer membrane protein VDAC and its interaction with antiapoptotic Bcl-xL", Biochemistry 46(2):514-525 (2007).

Olson and Kornbluth, "Mitochondria in apoptosis and human disease", Curr. Mol. Med., 1:91-122 (2001).

Peng et al., "Determination of the number of polypeptide subunits in a functional VDAC channel from *Saccharomyces cerevisiae*", J Bioenerg. Biomembr. 24:27-31 (1992).

Pillai and Panchagnula, "Polymers in drug delivery", Curr. Opin. Chem. Biol., 5(4):447-451 (2001).

Polgar et al., "Mutational analysis of ABCG2: role of the GXXXG motif", Biochemistry, 43:9448-9456 (2004).

Popp et al., "The role of the N and C termini of recombinant Neurospora mitochondrial porin in channel formation and voltage-dependent gating", J. Biol. Chem., 271(23):13593-13599 (1996).

Reymann et al., "Further evidence for multitopological localization of mammalian porin (VDAC) in the plasmalemma forming part of a chloride channel complex affected in cystic fibrosis and encephalomyopathy", Biochem Mol Med, 54(2):75-87 (1995).

Russ W.P. et al., "The GxxxG motif: a framework for transmembrane helix-helix association", J. Mol. Biol., 296(3):911-919 (2000).

Sapra and Allen, "Improved outcome when B-cell lymphoma is treated with combinations of immunoliposomal anticancer drugs targeted to both the CD19 and CD20 epitopes", Clin. Cancer Res. 10(7):2530-2537 (2004).

Shi et al., "Identification of the protein-protein contact site and interaction mode of human VDAC1 with Bcl-2 family proteins", Biochem. Biophys. Res. Comm., 305(4):989-996 (2003).

Shimizu S. et al., "Bcl-2 family proteins regulate the release of apoptogenic cytochrome c by the mitochondrial channel VDAC", Nature, 399(6735):483-487 (1999).

Shoshan-Barmatz and Gincel, "The voltage-dependent anion channel: characterization, modulation, and role in mitochondrial function in cell life and death", Cell Biochem Biophys., 39:279-292 (2003).

Shoshan-Barmatz et al., "Subcellular localization of VDAC in mitochondria and ER in the cerebellum", Biochem. Biophys. Acta., 1657(2-3):105-114 (2004).

Shoshan-Barmatz and Israelson, "The voltage-dependent anion channel in endoplasmic/sarcoplasmic reticulum: characterization, modulation and possible function", J. Membr. Biol., 204(2):57-66 (2005).

Shoshan-Barmatz et al., "The voltage-dependent anion channel (VDAC): function in intracellular signalling, cell life and cell death", Curr. Pharm. design., 12(18):2249-2270 (2006).

Stanley et al., "Peptide-specific antibodies as probes of the topography of the voltage-gated channel in the mitochondrial outer membrane of *Neurospora crassa*", J. Biol Chem., 270:16694-16700 (1995).

Tatton and Olanow, "Apoptosis in neurodegenerative diseases: the role of mitochondria", Biochim. Biophys. Acta., 1410(2)195-213 (1999).

Tracy, "Development and scale-up of a microsphere protein delivery system", Biotechnol. Prog., 14(1):108-115 (1998).

Tsujimoto and Shimizu, "The voltage-dependent anion channel: an essential player in apoptosis", Biochimie (Paris) 84(2-3):187-193 (2002).

Zaid H. et al., "The voltage-dependent anion channel-1 modulates apoptotic cell death", Cell Death Diff. 12(7):751-760 (2005).

Zalk et al., "Oligomeric states of the voltage-dependent anion channel and cytochrome c release from mitochondria", Biochem. J., 386(Pt. 1):73-83 (2005).

Zheng et al., "Essential role of the voltage-dependent anion channel (VDAC) in mitochondrial permeability transition pore opening and cytochrome c release induced by arsenic trioxide", Oncogene, 23(6):1239-1247 (2004).

Database Uniprot May 10, 2005, Jaaro H. et al.: "Probable voltage-dependent anion selective channel 2". XP002462029. Database accession No. Q56UF7.

* cited by examiner

```
HUMAN VDAC1  1  MAVPPTYADL  GKSARDVFTK  GYGFGLIKLD  LKTKSENGLE
MOUSE VDAC1  1  MAVPPTYADL  GKSARDVFTK  GYGFGLIKLD  LKTKSENGLE
RAT VDAC1    1  MAVPPTYADL  GKSARDVFTK  GYGFGLIKLD  LKTKSENGLE

FTSSGSANTE  TTKVTGSLET  KYRWTEYGLT  FTEKWNTDNT
                FTSSGSANTE  TTKVNGSLET  KYRWTEYGLT  FTEKWNTDNT
                FTSSGSANTE  TTKVNGSLET  KYRWTEYGLT  FTEKWNTDNT

LGTEITVEDQ  LARGLKLTFD  SSFSPNTGKK  NAKIKTGYKR
                LGTEITVEDQ  LARGLKLTFD  SSFSPNTGKK  NAKIKTGYKR
                LGTEITVEDQ  LARGLKLTFD  SSFSPNTGKK  NAKIKTGYKR

EHINLGCDMD  FDIAGPSIRG  ALVLGYEGWL  AGYQMNFETA
                EHINLGCDVD  FDIAGPSIRG  ALVLGYEGWL  AGYQMNFETS
                EHINLGCDVD  FDIAGPSIRG  ALVLGYEGWL  AGYQMNFETS

KSRVTQSNFA  VGYKTDEFQL  HTNVNDGTEF  GGSIYQKVNK
                KSRVTQSNFA  VGYKTDEFQL  HTNVNDGTEF  GGSIYQKVNK
                KSRVTQSNFA  VGYKTDEFQL  HTNVNDGTEF  GGSIYQKVNK

KLETAVNLAW  TAGNSNTRFG  IAAKYQIDPD  ACFSAKVNNS
                KLETAVNLAW  TAGNSNTRFG  IAAKYQVDPD  ACFSAKVNNS
                KLETAVNLAW  TAGNSNTRFG  IAAKYQVDPD  ACFSAKVNNS

SLIGLGYTQT  LKPGIKLTLS  ALLDGKNVNA  GGHKLGLGLE  FQA
                SLIGLGYTQT  LKPGIKLTLS  ALLDGKNVNA  GGHKLGLGLE  FQA
                SLIGLGYTQT  LKPGIKLTLS  ALLDGKNVNA  GGHKLGLGLE  FQA
```

N-TERMINAL VDAC VARIANTS AND USES THEREOF

RELATED APPLICATION DATA

This application is the U.S. national stage of PCT/IL2007/000455 filed on Apr. 10, 2007, which is based on and claims the benefit of U.S. Provisional Application No. 60/789,570 filed on Apr. 6, 2006, the content of each of which is expressly incorporated herein in its entirety by reference hereto.

FIELD OF THE INVENTION

The present invention relates to variants and variant peptides of the mitochondrial protein, voltage-dependent anion channel (VDAC) and to polynucleotides encoding same. In particular, the present invention is directed to N-terminal truncated and mutated VDAC proteins, mutated N-terminal derived peptides and nucleotide sequences thereof useful in inhibiting apoptosis, and to pharmaceutical compositions comprising same useful in the treatment of diseases associated with excessive and untimely apoptosis.

BACKGROUND OF THE INVENTION

Mitochondria and their Role in Apoptosis

Mitochondria are central to basic life functions, particularly the generation of cellular energy, and as such are the sites of key components of the biosynthetic pathways. Mitochondria are also potent integrators and coordinators of programmed cell death or apoptosis. The mitochondrion represents a discrete sub-cellular organelle that is comprised of about 1000 different protein species. One of these mitochondrial proteins controlling processes associated with both cell life and death is the voltage-dependent anion channel (VDAC).

The role of mitochondria in regulating cell death has been revealed and it is well accepted that mitochondria play a major role in regulating apoptosis (Kroemer et al. (1997). Immunol. Today 18, 44-51). Following an apoptotic stimulus, various proteins that normally reside in the intermembrane space of mitochondria, including cytochrome c and apoptosis-inducing factors, are released to the cytosol and initiate the activation of procaspases, the protease mediators of cell death. It remains unclear, however, how these apoptosis initiators cross the outer mitochondrial membrane (OMM) and are released to the cytosol. While some models predict that release occurs as a result of the swelling of the mitochondrial matrix with subsequent rupture of the OMM, other models predict the formation of a pore large enough to allow the passage of cytochrome c and other proteins into the cytosol, without compromising OMM integrity. The finding that cytochrome c can leak from intact mitochondria (see, for example, Doran and Halestrap (2000). Biochem J. 348 (Pt 2), 343-350) supports those models predicting the specific permeability of the OMM. VDAC, previously suggested to participate in the release of cytochrome c, is considered as a promising candidate for such an OMM pore-forming protein. Some of the inventors of the present invention and co-workers have shown that VDAC functions in the release of apoptotic-mediated proteins from the mitochondria and to interact with different apoptosis-regulators (Shoshan-Barmatz et al. (2006) Curr. Pharm. Design, 12, 2249-2270; Shoshan-Barmatz and Israelson (2005) J. Membr. Biol. 204, 57-66).

VDAC, the major OMM transporter, also plays an important role as a controlled passage of adenine nucleotides, $Ca^+$ and other metabolites into and out of mitochondria, thereby, may also function as a key protein in the energy production by mitochondria (Colombini (2004). Mol Cell Biochem 256-257 (1-2), 107-115).

VDAC: Structure-Function

Mammalian VDAC, also known as mitochondrial porin, is a 31 kDa protein with a large pore diameter of about 3.0 nm. VDAC has been purified and characterized by reconstitution into a planar lipid bilayer (PLB), and its conductance and ion selectivity were found to be voltage dependent (Shoshan-Barmatz and Gincel (2003) Cell Biochemistry and Biophysics 39, 279-292).

The molecular nature of VDAC gating mechanism has yet to be resolved. Computer modeling of the VDAC's primary amino acid sequences led to the development of models showing the transmembrane organization, consisting of a single amphipathic N-terminal α-helix and 13 or 16 transmembrane β-strands (Colombini (2004), supra; De Pinto et al. (2003) Ital. J. Biochem. 52, 17-24). These β-strands are connected by several peptide loops of different sizes on both sides of the membrane that serve as potential protein interacting sites. It is widely accepted that monomeric VDAC serves as the functional channel in *Saccharomyces cerevisiae* (Peng et al. (1992) Bioenerg Biomembr 24, 27-31). However, evidence, consistent with oligomerization of rat liver or *Neurospora crassa* purified VDAC, suggests that VDAC exists as a dimer, and possibly a tetramer (Krause et al. (1986) Biochim Biophys Acta, 860: 690-698). Using rat liver, brain mitochondria or recombinant human VDAC, the existence of VDAC dimers to tetramers was also reported (Zalk et al. (2005) Biochemical J. 386, 73-83; Shoshan-Barmatz et al. (2006) Curr. Pharm. Design, 12, 2249-2270).

Three mammalian isoforms of VDAC are known, VDAC1, VDAC2, VDAC3, where VDAC1 is the major isoform expressed in mammalian cells.

U.S. Pat. No. 5,780,235 discloses two novel VDAC sequences, which were named HACH (human voltage-dependent anion channel), subsequently identified as VDAC2 and VDAC3. That patent provides genetically engineered expression vectors, host cells containing the vector, a method for producing HACH, a method for identifying pharmaceutical compositions inhibiting the expression and activity of HACH and the use of such compositions for the treatment of cancer and proliferative diseases.

International Application Publication No. WO 2006/095347 to some of the inventors of the present invention discloses VDAC1 molecules capable of modulating apoptosis in a cell, the molecule selected from: (i) an isolated VDAC1 polypeptide variant having at least one amino acid substitution in an amino acid residue residing in a VDAC1 cytosolic domain and (ii) an isolated VDAC1 peptide fragment, analog, chemical derivative and a salt thereof, wherein the peptide fragment, analog, chemical derivative or salt thereof is derived from a VDAC1 cytosolic domain or partial sequence thereof. The amino acid sequences disclosed therein were shown to cause a dramatic increase in apoptosis of human cancer cell lines and in chemo- and radio-resistant cancer cells. A VDAC1 N-terminal domain peptide was disclosed as useful to enhance apoptosis.

All VDAC membranal topology predictions so far performed have emphasized the presence of a segment of α-helix, with amphipathic features, at the N-terminus of the protein. According to the three proposed models, the VDAC1 N-terminus amphipathic α-helix is either exposed to the cytoplasm (De Pinto et al. (2003). Ital. J. Biochem. 52, 17-24), crosses the membrane (Colombini (2004), Mol Cell Biochem 256-257, 107-115) or lies on the membrane surface (Reymann et al. (1995). Biochemical and Molecular Medicine, 54, 75-87). Although the N-terminal α-helix has been proposed to form part of the lumen facing the wall of the open state of the channel and shows some motion during voltage gating, the limited hydrophobicity of the sequence suggests it unlikely that this segment of VDAC is permanently embedded in the membrane.

Certain N-terminal variants of VDAC have been disclosed in the art. VDAC1 with N-terminal extensions display voltage-induced partial closures, while variants with an N-terminal region shortened by more than 6-7 amino acid residues exhibit a destabilized open state In addition, scVDACD1-8, the bacterially expressed truncated yeast variant lacking the first eight amino acids, behaves atypically in bilayer experiments: rather than forming stable open channels with discrete transitions to a lower subconductance level, scVDACD1-8 induces channels that flicker rapidly (Koppel et al. (1998). J. Biol. Chem. 273, 13794-800).

The role of the N and C-termini in channel formation was studied in *Neurospora crassa* VDAC (Popp et al. (1996). J. Biol. Chem. 271, 13593-13599). Wild-type and mutant porins from *Neurospora crassa* were expressed as His-tag fusion products. Mutants lacking part of the N-terminus (DeltaN2-12porin, DeltaN3-20porin), part of the C-terminus (DeltaC269-283porin), or both (DeltaN2-12/DeltaC269-283porin) showed channel-forming activity. A VDAC mutant or peptide useful for the inhibition of apoptosis was neither taught nor suggested. The N-terminal α-helix was shown to interact specifically with cytochrome c (Stanley et al. (1995). J Biol Chem 270, 16694-16700). In addition, it has also been suggested that the mobility of the α-helix may modulate the accessibility of the pro- and anti-apoptosis proteins Bax and Bcl-XL to their binding sites at the VDAC loop regions (Shi et al. (2003). Biochem Biophys Res Comm 305, 989-96). Thus, the accumulated evidence suggests that the N-terminal region of VDAC corresponds to a mobile component of the protein.

U.S. Patent Application Publication No. 20050234116 discloses a promoter of neurotrophin (nerve growth factor) production/secretion as a VDAC regulator, apoptosis suppressor or mitochondria function ameliorator, useful as an agent for the prophylaxis or treatment of Down's syndrome and the like.

U.S. Patent Application Publication No. 20060252822 provides a new class of compounds for the labeling and modulation of mitochondrial permeability transition pore (MPTP) in the sub μM range, wherein isoform 1 of VDAC (VDAC1) is identified as a MPTP component and as the molecular target of these compounds. That disclosure further provides methods for identifying an active agent that modulates the activity of the MPTP complex, specifically methods for identifying an active agent that modulates the activity of the MPTP complex by interacting with the VDAC1 component.

The Role of GXXXG Motifs in the Function of the N-Terminus of VDAC1

Association between monomers is mediated by helix-helix contacts involving specific amino acid residues. The GXXXG motif and "GXXXG-like" motifs (in which one or both glycine residues are substituted by other small amino acids) has been identified as one of the most frequently occurring transmembrane (TM) sequence motifs as a potential site for tight interaction between TM α-helices (Arselin et al. (2003). Eur J Biochem 270, 1875-1884). This motif is a potential site for tight interaction between α-helices as a result of a three amino acid residue separation between the glycine residues aligns them on one face of the helix, thus providing a flat platform for close binding of a partner α-helix (Polgar et al. (2004). Biochemistry 43, 9448-9456). The GXXXG motif has been linked with dimerization of proteins including glycophorin A, human carbonic anhydrase, yeast ATP synthase and more. In VDAC, the GXXXG motif is present in the N-terminus of the channel that forms an α-helix structure.

There remains an unmet need for therapeutic agents effective in inhibiting or decreasing apoptosis that may be useful for the treatment of variant diseases, including neurodegenerative, cardiac and ophthalmic diseases. The art neither teaches nor suggests an N-terminal VDAC variant polypeptide or peptides useful for promoting cell proliferation and or inhibiting apoptosis.

SUMMARY OF THE INVENTION

The present invention provides N-terminal variant VDAC molecules, their nucleotide sequences and compositions comprising same. The present invention also discloses the use of N-terminal variant VDAC molecules and N-terminal derived peptides in treating diseases and disorders associated with excess apoptosis.

Unexpectedly, it is now shown that expression of variant VDAC sequences having altered amino-terminal domain inhibits apoptotic cell death. Suitable N-terminal variant sequences include N-terminal truncated and N-terminal mutated VDAC polypeptides comprising an altered amino acid sequence derived from the mitochondrial VDAC protein. Specifically, the ectopic or exogenous expression of N-terminal truncated VDAC polypeptide or an N-terminal mutated VDAC polypeptide are able to restore cell growth and/or inhibit apoptosis. The present invention also discloses mutated VDAC N-terminal derived peptides that are capable of inhibiting apoptosis.

According to a first aspect, the present invention provides an isolated N-terminal VDAC variant molecule capable of inhibiting apoptosis in a cell, the molecule selected from the group consisting of an N-terminal truncated VDAC polypeptide, an N-terminal mutated VDAC polypeptide and a mutated VDAC N-terminal derived peptide, a fragment, analog, chemical derivative and a salt thereof.

In some embodiments the isolated N-terminal VDAC variant is derived from a VDAC1, VDAC2 or VDAC3 isoform. In one embodiment the variant derives from VDAC1. In specific embodiments the VDAC variant molecule is derived from human VDAC1 polypeptide.

In some embodiments the N-terminal truncated VDAC polypeptide is lacking an amino acid sequence comprising the α-helix domain. In some embodiments the polypeptide is lacking the α-helix domain comprising up to about 26 amino acids. In some embodiments the polypeptide is lacking the α-helix domain comprising up to about 20 amino acids. In some embodiments the VDAC polypeptide is lacking at least the GXXXG amino acid sequence.

In some currently preferred embodiments the N-terminal truncation extends from about 1 to 26-amino acids. In some embodiments the truncation extends from about 5 to about 26 amino acids, alternatively from about 10 to about 26 amino acids. According to one embodiment the N-terminal truncated VDAC is a human VDAC1 polypeptide having an amino acid sequence as set forth in SEQ ID NO: 1. The corresponding polynucleotide sequence is set forth in SEQ ID NO:2.

In another embodiment the N-terminal truncated VDAC is a mouse or rat VDAC1 polypeptide lacking amino acids 1-26, having an amino acid sequence as set forth in SEQ ID NO:3 and SEQ ID NO:5, respectively. The corresponding polynucleotide sequences are set forth in SEQ ID NO:4 and SEQ ID NO:6, respectively.

The N-terminal truncated VDAC1 polypeptide may comprise further structural changes including additional amino acid substitutions, amino acid deletions and additions. Accordingly the present invention provides a polypeptide variant having about 80%, about 85%, about 90% about 95%, about 98% or about 99% homology to any one of SEQ ID NO:1, SEQ ID NO:3 and SEQ ID NO:5.

In some embodiments the VDAC variant molecule is a VDAC polypeptide comprising a mutation in the N-terminal domain. The mutation can be an amino acid deletion, substitution or insertion. Preferably the mutation interferes with the α-helix structure. According to certain embodiments, the mutation is within the GXXXG amino acid sequence. According to certain currently preferred embodiments, the mutation is substitution of glycine (G) 21 to tryptophan (W). According to certain currently preferred embodiments, the N-terminal mutated VDAC molecule is mutated VDAC1 human protein (SEQ ID NO:33).

In specific embodiments, the mutated VDAC N-terminal derived peptide comprises up to about 26 consecutive amino acids, up to about 24 amino acids, up to about 22, up to about 20, up to about 15 amino acids, or up to about 10 amino acid residues.

It is to be understood that N-terminal peptides derived from native VDAC molecules are explicitly excluded from the present invention. Specifically, a native N-terminal derived VDAC peptide having amino acids 1-26 of human VDAC1 was disclosed in International Patent Application Publication No. WO2006/095347. That peptide, as is set forth in SEQ ID NO:34 and its corresponding nucleotide sequence as is set forth in SEQ ID NO:35 are excluded from the present invention.

According to certain currently preferred embodiment, the mutated N-terminal derived peptide comprises mutated α-helix domain. According to one embodiment, the mutation is within the amino acid sequence GXXXG. According to one currently preferred embodiment, the mutation is a substitution of Gly (G) with Trp (W) at position 21. According to one embodiment, the mutated N-terminal derived peptide has an amino acid sequence as set forth in SEQ ID NO:36.

In other embodiments, the VDAC variant derivative is an amidated derivative. In other embodiments the N-terminal variant proteins further comprises a cell penetrating peptide (CPP) or other sequence that enables cell penetration or polypeptide stabilization.

The present invention also encompasses fragments, analogs and derivatives of the N-terminal VDAC variant molecules.

In another aspect, the present invention provides isolated nucleotide sequences encoding an N-terminal VDAC variant polypeptide capable of inhibiting apoptosis in a cell. In one embodiment the VDAC is a VDAC1 protein and the nucleotide sequence is selected from the group consisting of the nucleic acid sequences set forth in any one of SEQ ID NO:2, SEQ ID NO:4, and SEQ ID NO:6. In another embodiment the present invention provides a polynucleotide encoding a polypeptide variant having about 80%, about 85%, about 90% about 95%, about 98% or about 99% homology to any one of SEQ ID NO:1, SEQ ID NO:3 SEQ ID NO:5. Polynucleotides having single nucleotide polymorphisms (SNPs) encoding variant VDAC polypeptides according to the present invention are specifically encompassed within the scope of the preset invention.

In another aspect the present invention provides a polynucleotide construct comprising a nucleic acid sequence encoding an N-terminal VDAC variant polypeptide capable of inhibiting apoptosis in a cell. The N-terminal VDAC1 variant encompasses N-terminal truncated VDAC1 polypeptide and N-terminal mutated VDAC1 polypeptide. In some embodiments the polynucleotide construct is an expression vector.

Further provided is a host cell comprising a polynucleotide construct comprising a nucleotide sequence encoding an N-terminal truncated or mutated VDAC polypeptide capable of inhibiting apoptosis in a cell.

According to another aspect the present invention provides a pharmaceutical composition comprising an N-terminal VDAC variant amino acid sequence according to the present invention and a pharmaceutically acceptable diluent or excipient. In some embodiments the pharmaceutical composition comprises an N-terminal truncated VDAC1 polypeptide sequence as set forth in any one of SEQ ID NO:1, SEQ ID NO:3 and SEQ ID NO:5.

In one embodiment the present invention further provides a pharmaceutical composition comprising an isolated nucleic acid sequence encoding an N-terminal truncated VDAC polypeptide, or an N-terminal mutated VDAC polypeptide of the invention. The present invention further encompasses polynucleotide constructs comprising the nucleic acid sequences according to the invention and host cells comprising said constructs.

In certain embodiments the pharmaceutical composition comprises an N-terminal VDAC variant amino acid sequence according to the present invention and a shielding derivative. In certain embodiments the shielding derivative comprises PEI, PEG and lipids.

In certain embodiments the pharmaceutical composition comprises an encapsulated VDAC sequence according to the present invention. In certain embodiments the VDAC sequence is an amino acid sequence. In other embodiments the VDAC sequence is a nucleic acid sequence encoded a VDAC polypeptide according to the present invention. In some embodiments the VDAC is encapsulated into a vesicle, or into liposomes.

In yet another aspect the present invention provides a method for treating a subject with a disorder or disease associated with excess apoptosis, the method comprising administering to a subject in need thereof a composition comprising a therapeutically effective amount of an agent selected from the group consisting of i) an N-terminal truncated VDAC polypeptide or an N-terminal mutated VDAC polypeptide or a mutated VDAC N-terminal derived peptide, a fragment, derivative or analog thereof and ii) a nucleic acid encoding an N-terminal truncated VDAC polypeptide or an N-terminal mutated VDAC polypeptide or a mutated VDAC N-terminal derived peptide.

In some embodiments the agent is an N-terminal truncated VDAC1 polypeptide selected from the group consisting of SEQ ID NO:1, SED ID NO:3 and SEQ ID NO:5. In other embodiments the agent is a nucleic acid encoding an N-terminal truncated VDAC1 polypeptide, the nucleic acid sequence selected from the group consisting of SEQ ID NO:2, SED ID NO:4 and SEQ ID NO:6.

In some embodiments the disease or disorder is selected from immunodeficiency diseases, including AIDS; senescence; neurodegenerative diseases including Alzheimer's Disease, Huntington's Disease, Parkinson's Disease or Amyotrophic Lateral Sclerosis (ALS); ischemia and reperfusion; infertility; wound-healing; stroke; myocardial infarction; cardiac disease, hypertension; septic shock; organ transplantation and ophthalmic diseases including diabetic retinopathy and age-related macular degeneration (AMD).

In another aspect the present invention provides a method of inhibiting apoptosis in a cell, the method comprising administering to the cell an isolated VDAC variant molecule selected from i) an N-terminal truncated VDAC polypeptide or an N-terminal mutated VDAC polypeptide, a fragment, derivative or analog thereof and ii) a nucleic acid encoding an N-terminal truncated VDAC polypeptide or an N-terminal mutated VDAC polypeptide.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1 shows an alignment of human, mouse and rat VDAC1 amino acid sequences as follows: Human VDAC1: SEQ ID NO:7; Mouse VDAC1: SEQ ID NO:10; and Rat VDAC1: SEQ ID NO: 13.

DETAILED DESCRIPTION OF THE INVENTION

Figure 2:
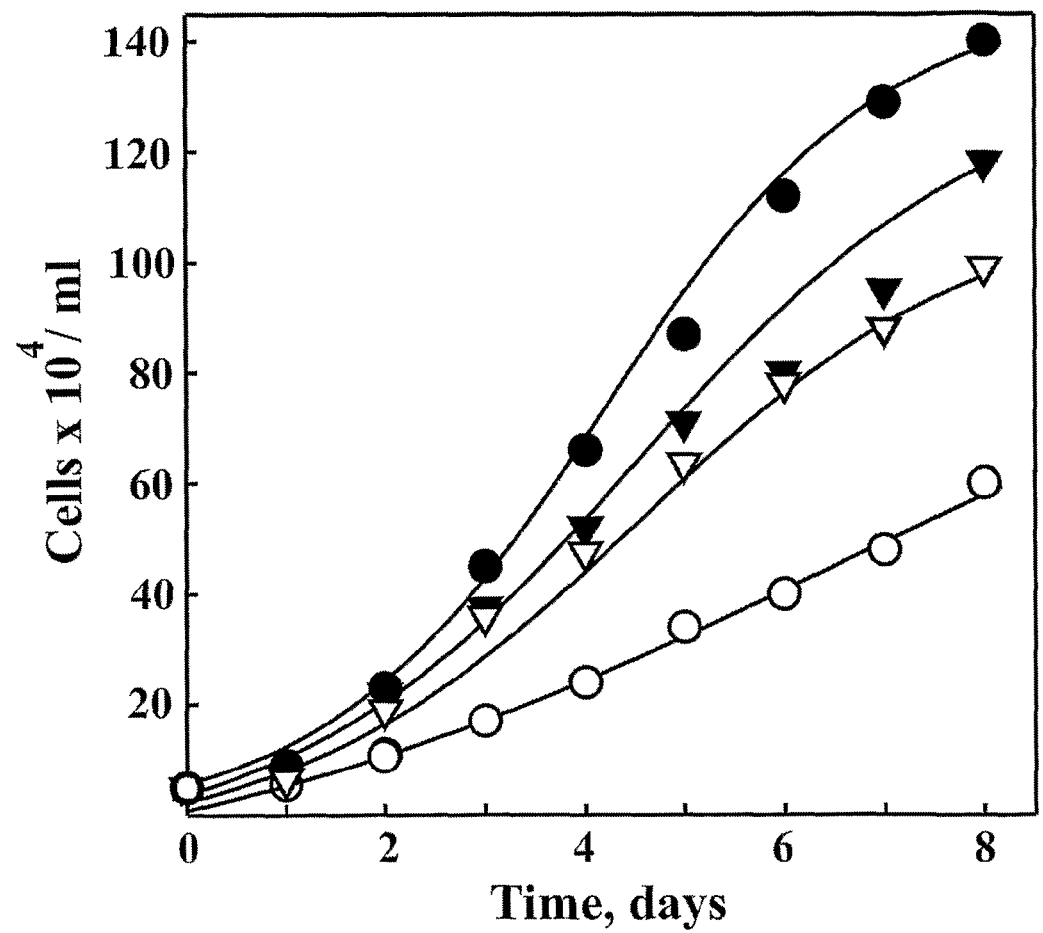
FIG. 2 shows restoration of cell growth and ATP levels by N-terminal truncated VDAC1 in T-REx-293 cells silenced for hVDAC1 expression by shRNA-hVDAC1, T REx-293 cells (●), T-REx-293 cells silenced for hVDAC1 expression by shRNA-hVDAC (○), native mVDAC (▼) and Δ1-26 mVDAC1 ( ) Cell growth rates were monitored utilizing Trypan-Blue staining; cells were counted under a microscope.

The present invention provides N-terminal VDAC polypeptide variants including N-terminal truncated, N-terminal mutated VDAC molecules as well as N-terminal mutated peptides, useful in preventing apoptotic cell death. The present invention also discloses use of the VDAC variants of the invention for treating diseases and disorders associated with excess apoptosis.

Without wishing to be bound to a specific theory or mechanism the N-terminal VDAC variants and N-terminal VDAC-based peptides are designed to interfere with the release of cytochrome c, which requires the N-terminal domain of the VDAC protein.

DEFINITIONS

For convenience certain terms employed in the specification, examples and claims are described herein.

The term "VDAC" as used herein and in the claims refers to the VDAC isoforms, VDAC1, VDAC2 and VDAC3, of a highly conserved family of mitochondrial porin and the corresponding polynucleotides. Four VDAC isoforms, encoded by three genes, are known to date.

Alignment of the protein sequences of the human, mouse and rat VDAC1 isoform are provided in FIG. 1.

Human VDAC1 set forth in SEQ ID NO:7, (NP_003365) is a 283 amino acid protein; Human VDAC2 set forth in SEQ ID NO:8 (NP_003366) is a 294 amino acid protein; Human VDAC3 set forth in SEQ ID NO:9 (NP_005653) is a 283 amino acid protein.

Mouse VDAC1 is set forth in SEQ ID NO:10 (NP_035824); Mouse VDAC2 is set forth in SEQ ID NO:11 (NP_035825); Mouse VDAC3 is set forth in SEQ ID NO:12 (NP_035826).

Rat VDAC1 is set forth in SEQ ID NO:13 (NP_112643); Rat VDAC2 is set forth in SEQ ID NO:14 (NP_112644); Rat VDAC3 is set forth in SEQ ID NO:15 (NP_112645).

The corresponding polynucleotide sequences are set forth in SEQ ID NO:16-SEQ ID NO:24. The polynucleotide sequences of Human VDAC1, VDAC2 and VDAC3 having accession numbers NM_003374, NM_003375 and NM_005662 are set forth in SEQ ID NO:16-SEQ ID NO:18 respectively. The polynucleotide sequences of mouse VDAC1, VDAC2 and VDAC3 having accession numbers NM_011694, NM_011695 and NM_011696 are set forth in SEQ ID NO:19-SEQ ID NO:21, respectively. The polynucleotide sequences of rat VDAC1, VDAC2 and VDAC3 having accession numbers NM_031353, NM_031354 and NM_031355 are set forth in SEQ ID NO:22-SEQ ID NO:24, respectively.

The term "VDAC N-terminal domain" refers to amino acid sequences that make up the amino terminal region of the polypeptide. The N-terminal domains of human VDAC1, 2 and 3, include amino acids 1 to about 26, of each respective polypeptide. An "N-terminal truncated VDAC variant" encompasses VDAC polypeptides in which all or part of the N-terminal domain is absent. An N-terminal truncated variant includes polypeptides lacking between 6 and 26 amino acids from the N-terminal domain. One currently preferred N-terminal domain variant is a human VDAC1 variant lacking amino acids 1-26, the amino acid sequence of this N-terminal truncated protein is set forth in SEQ ID NO:1.

```
    IKLD LKTKSENGLE FTSSGSANTE TTKVTGSLET
KYRWTEYGLT FTEKWNTDNT LGTEITVEDQ LARGLKLTFD
SSFSPNTGKK NAKIKTGYKR EHINLGCDMD FDIAGPSIRG
ALVLGYEGWL AGYQMNFETA KSRVTQSNFA VGYKTDEFQL
HTNVNDGTEF GGSIYQKVNK KLETAVNLAW TAGNSNTRFG
IAAKYQIDPD ACFSAKVNNS SLIGLGYTQT LKPGIKLTLS
ALLDGKNVNA GGHKLGLGLE FQA
```

The corresponding nucleotide sequence is set forth in SEQ ID NO:2.

The term "N-terminal mutated VDAC variant" encompasses VDAC polypeptides in which the VDAC N-terminal domain contains at least one mutation. The mutation can be an amino acid deletion, substitution or insertion. According to certain embodiments of the present invention, the mutation is within the GXXXG motif.

Throughout the specification and claims that follow, the terms "VDAC polypeptide" and "VDAC protein" are used interchangeably. The term "VDAC peptide" refers to a peptide derived from a mutated VDAC protein, comprising amino acid sequence of up to about 70 amino acid residues, up to about 60 amino acid residues, up to about 40 amino acid residues, preferably from about 15 to about 30 amino acid residues in length. In preferred embodiments the peptides are derived form the N-terminal domain of the VDAC1 protein.

As used herein the term "apoptosis" or "apoptotic cell death" refers to programmed cell death which can be characterized by cell shrinkage, membrane blebbing and chromatin condensation culminating in cell fragmentation. Cells undergoing apoptosis also display a characteristic pattern of DNA cleavage. Alternatively, apoptosis can be characterized indirectly by changes in the activity or expression of members of the apoptotic pathway, e.g. increased mitochondrial release of cytochrome c.

The term "expression vector" and "recombinant expression vector" as used herein refers to a DNA molecule containing a desired coding sequence and appropriate nucleic acid sequences necessary for the expression of the operably linked coding sequence in a particular host organism. The expression vector may comprise sequences encoding heterologous domains including but not limited to protein detection, purification or cleavage sequences that may be fused at the N- or C-terminus to the desired coding sequence, to yield a fusion protein. It is contemplated that the present invention encompasses expression vectors that are integrated into host cell genomes, as well as vectors that remain unintegrated into the host genome.

Any vector selected can be constructed such that it is capable of being transferred into the cells of interest either with or without VDAC amino acid sequence. Methods for manipulating the vector nucleic acid are well known in the art and include for example direct cloning and site-specific recombination using recombinases. In this manner, an expression vector can be constructed such that it can be replicated in any desired cell, expressed in any desired cell, and can even become integrated into the genome of any desired cell.

The term "expression product" is used herein to denote a VDAC amino acid sequence, according to the sequences of the present invention. A VDAC expression product is preferably a translation product, or a fragment of translation product from any one or more of the N-terminal VDAC variant polypeptides or peptides.

The term "exogenous" is used herein refers to a VDAC amino acid sequence which is introduced into a cell. For example, "exogenous VDAC1 amino acid sequence" should be construed to include a VDAC1 amino acid sequence expressed from a nucleic acid, which has been introduced into a cell using recombinant technology, a VDAC1 amino acid sequence that is added to a cell and any and all combinations thereof. Therefore, the term should not be construed to be limited solely to the addition of VDAC1 amino acid sequence to a cell per se, but should be expanded to include the expression of VDAC1 amino acid sequence in a cell when the VDAC1 amino acid sequence is expressed from a nucleic acid, which has been introduced into the cell.

Throughout the specification and the claims that follow, the terms "VDAC polypeptide", "VDAC peptide", "VDAC" peptidomimetic" "VDAC polypeptide or peptide analog" and the like refers to molecules having a sequence which is a VDAC amino acid or a variant thereof, or a sequence derived from the VDAC family of proteins. Within the context of the present invention, a VDAC amino acid sequence can be or comprise one or more amino acid residue insertions, deletions, or substitutions. Preferably, any substitution is conservative in that it minimally disrupts the biochemical properties of the VDAC amino acid sequence polypeptide. Given the properties of the subject amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved. Additionally, all or a part of the amino acids may be substituted with the D isoform of amino acids.

According to one aspect, the present invention provides an isolated N-terminal VDAC variant molecule capable of inhibiting apoptosis in a cell, the molecule selected from the group consisting of an N-terminal truncated VDAC polypeptide and an N-terminal mutated VDAC polypeptide, a fragment, analog, chemical derivative and a salt thereof. According to another aspect, the present invention provides nucleic acid sequences encoding the N-terminal variant molecules of the invention.

Figure 10A:
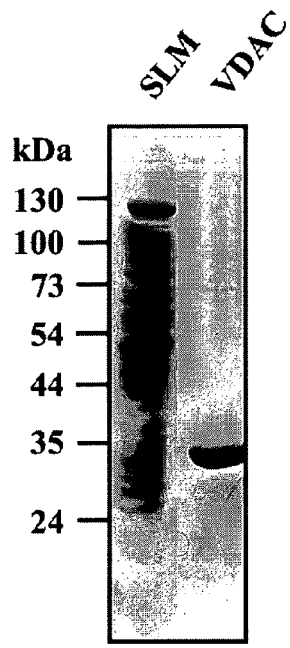
FIG. 10 shows immunostaining of VDAC purified from sheep liver mitochondria (FIG. 10A) and a schematic wheel diagram of the VDAC N-terminus (FIG. 10B. The diagram was created by a Java applet written by Edward K. O'Neil and Charles M. Grisham (University of Virginia in Charlottesville, Va.).
Figure 10B:
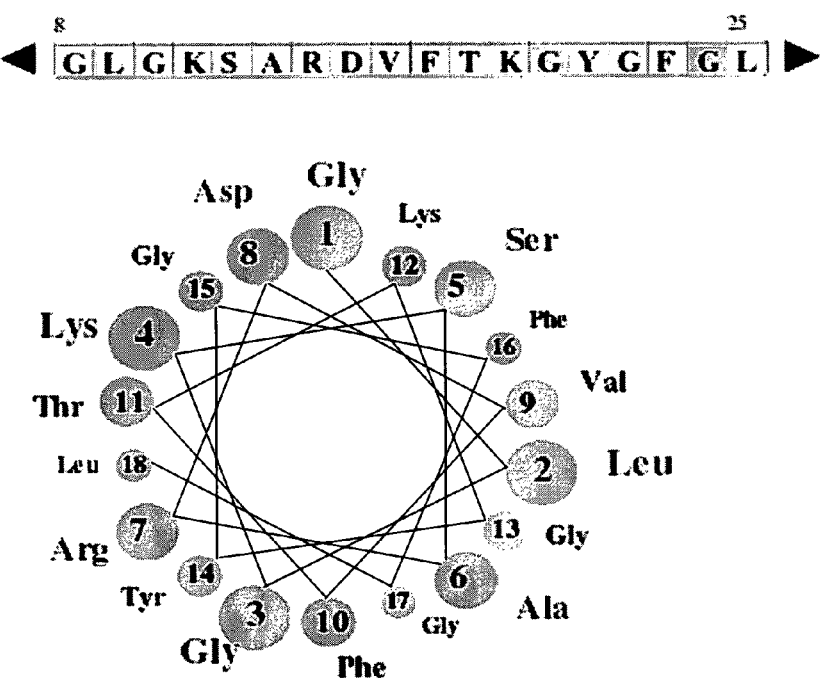
Figure 11:
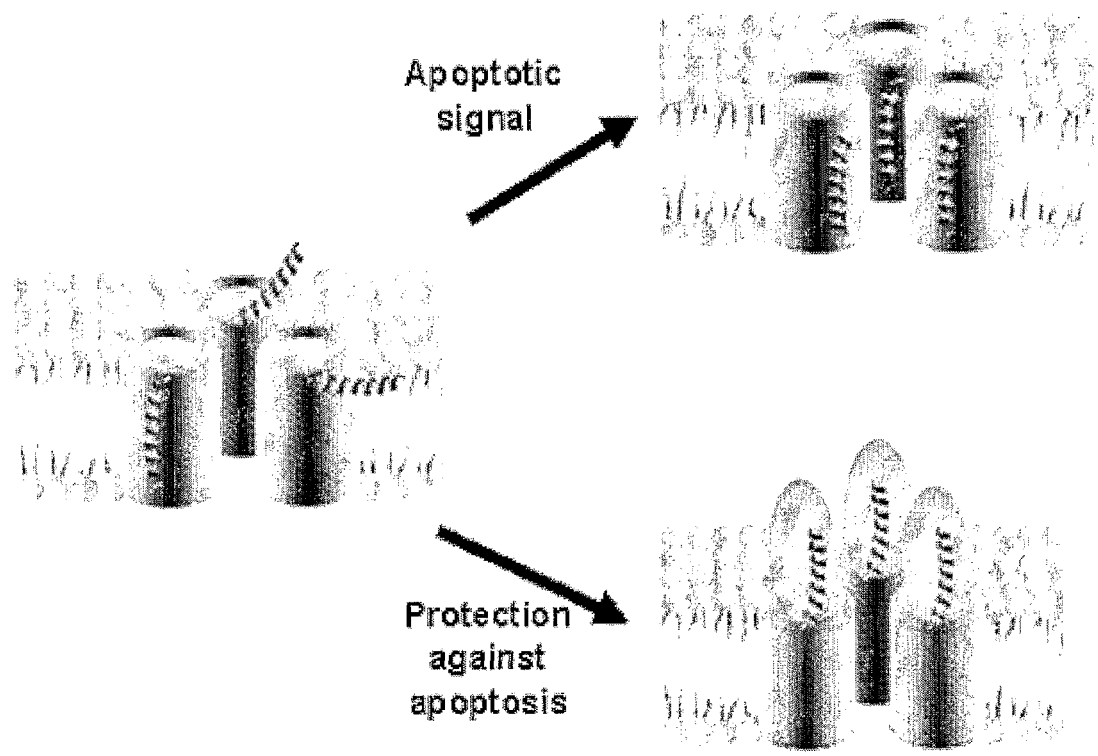
FIG. 11 shows a proposed model for VDAC1-N-terminous-mediating cytochrome c release. Side view across oligomeric VDAC1 forming a large pore in which the amphipathic α helix N-terminal of each VDAC1 molecule is freely mobilized (FIG. 11A). Upon an apoptotic signal, the amphipathic α helix N-terminal of each VDAC1 molecule in the oligomeric VDAC1 is flipping inside the hydrophobic pore formed by the β-barrels, forming hydrophilic pore capable of conducting cytochrome c release (FIG. 11B). The flipping of the a helix N-terminal inside the pore formed by VDAC1 molecules may be controlled by conditions leading to cytochrome c release, such as $Ca^{2+}$ overload or reactive oxygen species (ROS) and by anti-apoptotic (HK-I, Bcl2) interaction with it (FIG. 11C).

The present invention now shows that the N-terminal domain of VDAC1 polypeptides is essential for apoptosis and thus expressing in cells VDAC variants in which the N-terminal is absent or mutated can render these cells resistant to apoptosis. Without wishing to be bound to a certain theory or mechanism, the anti-apoptotic activity of the N-terminal VDAC variants may be attributed to the inability of the variants to mediate release of cytochrome c from the mitochondria into the cell, a key initial step in the apoptotic process. Relying on those models proposing that the delivery of apoptotic proteins across the outer mitochondrial membrane (OMM) is mediated by VDAC, the VDAC protein-conducting channel may be formed via oligomerization of VDAC, alone or together with other proapoptotic proteins. In biochemical assays, VDAC was shown to assume oligomeric forms (Zalk et al., (2005). Biochem J 386 (Pt 1), 73-83), while a recent NMR study found VDAC1 to exist as a trimer (Malia and Wagner (2007). Biochemistry 46 (2), 514-525). However, oligomerization of the VDAC1 β-barrels would form a hydrophobic channel unless the amphipathic α-helix N-terminal region of each VDAC1 molecule participated in pore formation by flipping inwards to line the formed pore (FIG. 10). According to this model the now hydrophilic pore would allow transport of charged proteins, including cytochrome c. By using N-terminally truncated VDAC1 the present invention now shows for the first time that the N-terminal domain of VDAC proteins is necessary for the release of cytochrome c and apoptosis, and that N-terminal truncated or mutated VDAC molecules inhibit apoptosis.

The present invention shows that the apart from inducing apoptosis, the N-terminal truncated VDAC1 is as functional protein as the native protein. As exemplified hereinbelow, expression of Δ(1-26)mVDAC1, as induced by either low or high tetracycline concentrations, restored cell growth in hVDAC1-shRNA-T-REx-293 cells silenced for human VDAC1. In addition bilayer-reconstituted truncated VDAC1 possesses channel properties as native one, although modified voltage dependence has been reported for the yeast or human recombinant proteins. Thus, the N-terminus is not required or involved in the transport activity of VDAC1 that is essential for cell growth.

Accordingly, the present invention also provides pharmaceutical formulations, both for veterinary and for human medical use, which comprise as the active agent one or more of the VDAC polypeptide variants, peptides, derivatives, analogs or salts thereof or a polynucleotide encoding same described in the invention, for the manufacture of a medicament for the treatment or prophylaxis of the diseases and disorders associated with excess apoptosis as described herein.

As exemplified hereinbelow, the N-terminal domain of VDAC1 protein is necessary for the binding of the anti-apoptotic proteins, Hexokinase 1 (HK-1) and Bcl2. Moreover, the present invention shows for the first time that a peptide derived from the N-terminal domain of VDAC1 protein strongly and specifically binds to immobilized HK-1 and Bcl2. These results support the findings that the N-terminal domain of VDAC1 is necessary for cytochrome c release associated with apoptosis.

Polypeptides, Peptides, Derivatives and Analogs

An "amino acid sequence", as used herein, refers to an oligopeptide, peptide, or polypeptide sequence, and fragments thereof, and to naturally occurring, recombinant or synthetic molecules. The term "polypeptide" refers to any chain of amino acids, regardless of length or post-translational modification (for example, glycosylation or phosphorylation).

The polypeptides, derivatives analogs and salts thereof comprise a variant VDAC amino acid sequence of up to about 400 amino acid residues, preferably up to about 300 amino acid residues, more preferably up to about 260 amino acid residues in length.

The peptides, derivatives analogs and salts thereof comprising a VDAC N-terminal mutated amino acid sequence can be of up to about 70 amino acid residues, up to about 60 amino acid residues, up to about 40 amino acid residues, preferably from about 15 to about 30 amino acid residues in length.

The terms "polypeptide" or "polypeptide fragment" as used herein are meant to encompass natural, non-natural and/or chemically modified amino acid residues connected one to the other by peptide or non-peptide bonds. Therefore the terms "polypeptide" and "peptide" includes a fragment, analog, derivative or a salt thereof. The amino acid residues are represented throughout the specification and claims by either one or three-letter codes, as is commonly known in the art. The compounds of the invention include linear and cyclic peptides and derivatives and analogs thereof.

The term "fragment" as used herein refers to a polypeptide or peptide having one or more deletions of amino acid residues relative to the sequences listed herein, so long as the requisite activity is maintained. The amino acid residues may be deleted from the amino terminus and/or carboxy terminus and/or along the peptide sequence.

Peptide fragments can be produced by chemical synthesis, recombinant DNA technology, or by subjecting the polypeptides and peptides listed herein to at least one cleaving agent. A cleaving agent can be a chemical cleaving agent, e.g., cyanogen bromide, or an enzyme, e.g., an exoproteinase or endoproteinase. Endoproteinases that can be used to cleave the peptides of the invention include trypsin, chymotrypsin, papain, V8 protease or any other enzyme known in the art to produce proteolytic fragments.

The terms "analog" and "derivative" refer to a peptide or polypeptide comprising at least one altered amino acid residue by an amino acid substitution, addition, deletion, or chemical modification, as compared with the native peptide. Polypeptide and peptide analogs particularly include amino acid substitutions and/or additions with non-natural amino acid residues, and chemical modifications, which do not occur in nature. Polypeptide or peptide analogs include variants and mimetics. A polypeptide or peptide mimetic or "peptidomimetic" is a molecule that mimics the biological activity of a polypeptide or peptide but is not completely peptidic in nature. Whether completely or partially non-peptide, peptidomimetics according to this invention provide a spatial arrangement of chemical moieties that closely resembles the three-dimensional arrangement of groups in the peptide on which the peptidomimetic is based. As a result of this similar active-site geometry, the peptidomimetic has effects on biological systems, which are similar to the biological activity of the peptide.

Polypeptide and peptide derivatives particularly include amino acid substitutions and/or additions with naturally occurring amino acid residues, and chemical modifications such as, for example, enzymatic modifications, typically present in nature. Accordingly, the present invention encompasses both derivatives and analogs of the VDAC polypeptides.

The present invention encompasses VDAC polypeptide and peptide derivatives or analogs of which at least one amino acid has been chemically modified. Chemical modifications of amino acid residues include, but are not limited to, amidation, methylation, acetylation, glycosylation, oxidation, reduction, myristylation, sulfation, acylation, ADP-ribosylation, cyclization, hydroxylation, iodination, derivatization by protecting/blocking groups, or any other derivatization method known in the art. Such alterations, which do not destroy, but may improve the VDAC variant biological activity, can occur anywhere along the sequence of the VDAC polypeptide, including at the polypeptide backbone, the amino acid side-chains, and at the amino or carboxyl termini.

By using "amino acid substitution", it is meant that an amino acid residue is substituted for a residue within the sequence resulting in a functionally equivalent or in a functionally different variant. The term "functionally equivalent" means, for example, a group of amino acids having similar polarity, similar charge, or similar hydrophobicity. For example, one or more amino acid residues within the sequence can be substituted by another amino acid of a similar polarity, which acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid (aspartate and glutamate). Such substitutions are known as conservative substitutions.

Additionally, a non-conservative substitution can be made in an amino acid that does not contribute to the biological activity of the polypeptide. Such non-conservative substitutions are also encompassed within the term "amino acid substitution", as used herein. It will be appreciated that the present invention further encompasses VDAC polypeptide derivatives or analogs, wherein at least one amino acid is substituted by another natural or non-natural amino acid to produce a polypeptide derivative or analog having increased stability or higher half life as compared to the native VDAC peptide fragment.

The present invention encompasses polypeptide and peptide hydrates and includes, but is not limited to, hemihydrate, monohydrate, dihydrate, trihydrate, and the like.

One aspect of the present invention provides a VDAC polypeptide or peptide further comprising a moiety that facilitates cell penetration. In one embodiment the moiety is a cell penetrating peptide (CPP). CPP's are typically amphipathic or cationic oligopeptides able to transport attached cargoes across cell membranes. In one embodiment the CPP comprises a fragment of the Drosophila antennapedia homeodomain (ANTP), comprising an amino acid sequence as set forth in SEQ ID NO:25.

SEQ ID NO:25: 5' MRQIKIWFQNRRMKWKK which is encoded by a nucleotide set forth in SEQ ID NO:26: 5' ATG CGT CAG ATT AAA ATT TGG TTT CAG AAT CGT CGT ATG AAA TGG AAA AAA.

One aspect of the present invention provides for a polypeptide analog such as a peptidomimetic, which mimics the structural features of the critical minimal epitope.

There are clear advantages for using a mimetic of a given peptide or polypeptide rather than the protein itself, since peptidic drugs often exhibit two undesirable properties: poor bioavailability and short duration of action. Peptide mimetics offer a route around these two major obstacles; since the molecules concerned have a long duration of action. Furthermore there are problems associated with stability, storage and immunoreactivity for peptides that are not experienced with peptide mimetics.

The design of the peptidomimetics may be based on the three-dimensional structure of VDAC alone or in complex with another protein. Interaction with the peptidomimetic can either induce an interacting protein to carry out the normal function caused by such binding (agonist) or disrupts such function (antagonist, inhibitor).

A primary goal in the design of peptide mimetics has been to reduce the susceptibility of mimics to cleavage and inactivation by peptidases. In one approach, one or more amide bonds are replaced in an essentially isosteric manner by a variety of chemical functional groups. In another approach, a variety of uncoded or modified amino acids such as D-amino acids and N-methyl amino acids are used to modify mammalian peptides. Alternatively, a presumed bioactive conformation is stabilized by a covalent modification, such as cyclization or by incorporation of γ-lactam or other types of bridges as disclosed for example in U.S. Pat. No. 5,811,392. In U.S. Pat. No. 5,552,534, non-peptide compounds are disclosed which mimic or inhibit the chemical and/or biological activity of a variety of peptides. Such compounds can be produced by appending to certain core species, such as the tetrahydropyranyl ring, chemical functional groups, which cause the compounds to be at least partially cross-reactive with the peptide. As will be recognized, compounds that mimic or inhibit peptides are to varying degrees cross-reactive therewith. Other techniques for preparing peptidomimetics are disclosed in U.S. Pat. Nos. 5,550,251 and 5,288,707, for example. Non-limiting examples of the use of peptidomimetics in the art include inhibitors of protein isoprenyl transferases (particularly protein farnesyltransferase and geranylgeranyltransferase) and anti-cancer drugs (U.S. Pat. No. 5,965,539) inhibitors of p21 ras (U.S. Pat. No. 5,910,478) and inhibitors of neurotropin activity (U.S. Pat. No. 6,291,247).

Whenever N-terminal VDAC variants are mentioned in the invention, also salts and functional derivatives thereof are contemplated, as long as they are able to inhibit apoptosis of a target cell. Thus, the present invention encompasses polypeptides containing non-natural amino acid derivatives or non-protein side chains.

The term "derivative" includes any chemical derivative of the variants of the invention having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. For example, free carboxyl groups may be derivatized to form salts, methyl and ethyl esters or other types of esters or hydrazides; free hydroxyl groups may be derivatized to form O-acyl or O-alkyl derivatives; the imidazole nitrogen of histidine may be derivatized to form N-im-benzylhistidine. The C-terminus of the peptide of the invention may be presented in the free carboxy form or, preferably, it is amidated to facilitate the synthesis and increase the stability of the polypeptide, for example to increase the resistance of the polypeptides to enzymatic cleavage in the organism, or modified in a way that increases its solubility.

Also included as chemical derivatives are those polypeptides which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted for serine; and ornithine may be substituted for lysine.

In addition, a VDAC polypeptide can differ from the natural VDAC sequence of the invention by chemical modifications including, but are not limited to, terminal-$NH_2$ acylation, acetylation, or thioglycolic acid amidation, and by terminal-carboxylamidation, e.g., with ammonia, methylamine, and the like. Peptides can be linear, cyclic or branched and the like, which conformations can be achieved using methods well known in the art.

Addition of amino acid residues may be performed at either terminus of the polypeptides or peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

Peptide Synthesis

The peptides, peptide derivatives and analogs of the invention may be synthesized using any recombinant or synthetic method known in the art, including, but not limited to, solid phase (e.g. Boc or f-Moc chemistry) and solution phase synthesis methods. For solid phase peptide synthesis, a summary of the many techniques may be found in Stewart and Young, 1963 (Prog Med. Chem. 19, 187-260); and Meienhofer and Atherton 1973 (Adv Appl Microbiol, 16, 203-300). For a review of classical solution synthesis, see Schroder and Lupke, 1965 (The Peptides, Vol. 1, Academic Press (New York).

The amino acid residues described herein are preferred to be in the "L" isomeric form. However, residues in the "D" isomeric form can be substituted for any L-amino acid residue, as long as the peptide substantially retains the desired functional property. Use of "D" amino acids may be used as is known in the art to increase the stability or half-life of the resultant peptide.

The term "α-helix domain" refers to a protein or polypeptide domain characterized by a single, spiral chain of amino acids stabilized by hydrogen bonds. In an amphipathic α-helix, one side of the helix contains mainly hydrophilic amino acids and the other side contains mainly hydrophobic amino acids. The amino acid sequence of amphipathic α-helix alternates between hydrophilic and hydrophobic residues every 3 to 4 residues, since the a helix makes a turn for every 3.6 residues.

The "GXXXG" and AXXXA motifs are frequently occurring sequences of residues that are known to favor helix-helix interactions in membrane proteins, as described hereinabove.

Nucleic Acids

In another aspect, the invention provides nucleic acid molecules encoding the native or mutated VDAC polypeptide or peptides of the invention.

The nucleic acid molecules may include DNA, RNA, or derivatives of either DNA or RNA. An isolated nucleic acid sequence encoding a polypeptide or a peptide can be obtained from its natural source, for example as a portion of a gene. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, comprising, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide of the present invention.

A nucleic acid molecule homolog can be produced using a number of methods known to those skilled in the art (see, for example, Sambrook et al. (1989). Molecular Cloning: A Laboratory Manual, 2d edition, Cold Spring Harbor Press). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologs can be also selected from a mixture of modified nucleic acids by screening for the function of the protein encoded by the nucleic acid.

A polynucleotide or oligonucleotide sequence can be deduced from the genetic code of a protein, however, the degeneracy of the code must be taken into account, and nucleic acid sequences of the invention also include sequences, which are degenerate as a result of the genetic code, which sequences may be readily determined by those of ordinary skill in the art.

The terms "nucleic acid" and "polynucleotide" and "nucleotide sequence" as used herein refer to an oligonucleotide, polynucleotide or nucleotide and fragments or portions thereof, and to DNA or RNA of genomic or synthetic origin, which may be single- or double-stranded, and represent the sense or antisense strand. The term should also be understood to include, as equivalents, analogs of either RNA or DNA made from nucleotide analogs, and, as applicable to the embodiment being described.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomer", and "probes", as commonly defined in the art.

As used herein, highly stringent conditions are those, which are tolerant of up to about 5% to about 25% sequence divergence, preferably up to about 5% to about 15%. Without limitation, examples of highly stringent, (10° C. below the calculated Tm of the hybrid) conditions use a wash solution of 0.1×SSC (standard saline citrate) and 0.5% SDS at the appropriate Ti (incubation temperature) below the calculated Tm of the hybrid. The ultimate stringency of the conditions is primarily due to the washing conditions, particularly if the hybridization conditions used are those, which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5×Denhardt's reagent, 0.5% SDS, 100 μg/ml denatured, fragmented salmon sperm DNA at an appropriate incubation temperature Ti. (See generally Sambrook et al., supra) for suitable high stringency conditions.

Stringency conditions are a function of the temperature used in the hybridization experiment and washes, the molarity of the monovalent cations in the hybridization solution and in the wash solution(s) and the percentage of formamide in the hybridization solution. In general, sensitivity by hybridization with a probe is affected by the amount and specific activity of the probe, the amount of the target nucleic acid, the detectability of the label, the rate of hybridization, and the duration of the hybridization. The hybridization rate is maximized at a Ti of 20-25° C. below Tm for DNA:DNA hybrids and 10-15° C. below Tm for DNA:RNA hybrids. It is also maximized by an ionic strength of about 1.5M $Na^+$. The rate is directly proportional to duplex length and inversely proportional to the degree of mismatching.

Specificity in hybridization, however, is a function of the difference in stability between the desired hybrid and "background" hybrids. Hybrid stability is a function of duplex length, base composition, ionic strength, mismatching, and destabilizing agents (if any).

The Tm of a perfect hybrid may be estimated for DNA: DNA hybrids using the equation of Meinkoth et al (1984), as $$Tm=81.5°\ C.+16.6(\log M)+0.41\ (\%\ GC)-0.61\ (\%\ \text{form})-500/L$$

and for DNA:RNA hybrids, as $$Tm=79.8°\ C.+18.5(\log M)+0.58\ (\%\ GC)-11.8\ (\%\ GC)^2-0.56\ (\%\ \text{form})-820/L$$

where M, molarity of monovalent cations, 0.01-0.4 M NaCl,

% GC, percentage of G and C nucleotides in DNA, 30%-75%,

% form, percentage formamide in hybridization solution, and

L, length hybrid in base pairs.

Tm is reduced by 0.5-1.5° C. (an average of 1° C. can be used for ease of calculation) for each 1% mismatching. The Tm may also be determined experimentally. As increasing length of the hybrid (L) in the above equations increases the Tm and enhances stability, the full-length rat gene sequence can be used as the probe.

Filter hybridization is typically carried out at 68° C., and at high ionic strength (e.g., 5-6×SSC), which is non-stringent, and followed by one or more washes of increasing stringency, the last one being of the ultimately desired high stringency. The equations for Tin can be used to estimate the appropriate Ti for the final wash, or the Tm of the perfect duplex can be determined experimentally and Ti then adjusted accordingly.

As used herein, "single nucleotide polymorphism" (SNP) is a single base pair change. A single nucleotide polymorphism occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphism can also arise from a deletion of a nucleotide or an insertion of a nucleotide relative to a reference allele. It should be noted that a single nucleotide change could result in the destruction or creation of a restriction site. Therefore it is possible that a single nucleotide polymorphism might also present itself as a restriction fragment length polymorphism. Furthermore, an SNP can lead to the formation of a variant protein due to a change in the encoded amino acid, splicing point etc.

The present invention further includes a nucleic acid sequence of the present invention operably linked to one or more transcription control sequences to form a recombinant molecule. The phrase "operably linked" refers to linking a nucleic acid sequence to a transcription control sequence in a manner such that the molecule is able to be expressed when transfected (i.e., transformed, transduced or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in animal, bacteria, helminth, yeast and insect cells.

A nucleic acid molecule of the invention may be inserted into appropriate expression vector, i.e., a vector which contains the necessary elements for the transcription and translation of the inserted coding sequence.

Constitutive promoters suitable for use with the present invention are promoter sequences that are active under most environmental conditions and most types of cells, such as the cytomegalovirus (CMV) and Rous sarcoma virus (RSV). Inducible promoters suitable for use with the present invention include for example the tetracycline-inducible promoter.

Vectors can be introduced into cells or tissues by any one of a variety of known methods within the art, including in vitro recombinant DNA techniques, synthetic techniques, and in vivo genetic recombination. Such methods are generally described in Sambrook et al., Molecular Cloning: A Laboratory Manual, Cold Springs Harbor Laboratory, New York 1989, 1992; in Ausubel et al., Current Protocols in Molecular Biology, John Wiley and Sons, Baltimore, Md. 1989.

It will be appreciated that the nucleic acid construct of the present invention can also utilize VDAC homologues, which exhibit the desired activity (i.e. inhibition of apoptosis) can be, for example, at least about 75%, 80%, 85%, 90%, 95%, 96%, 97%, 98%, 99% or more identical to a nucleotide sequence encoding a protein of the invention (e.g., to the entire length of the nucleotide sequence encoding the protein), or a biologically active portion or complement of any of these nucleotide sequences as determined using the BestFit software of the Wisconsin sequence analysis package, utilizing the Smith and Waterman algorithm.

The nucleic acid construct (also referred to herein as an "expression vector") of the present invention includes additional sequences that render this vector suitable for replication and integration in prokaryotes, eukaryotes, or preferably both (e.g., shuttle vectors). A typical cloning vector may also contain transcription and translation initiation sequences, transcription and translation terminators, and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated. Enhancer elements can stimulate transcription from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus or human or murine cytomegalovirus (CMV) and the long tandem repeats (LTRs) from various retroviruses, such as murine leukemia virus, murine or Rous sarcoma virus, and HIV. In constructing the expression vector, the promoter can be accommodated at various distances from the transcription start site without loss of promoter function.

Polyadenylation sequences can also be added to the expression vector in order to increase the efficiency of VDAC1 mRNA translation, including a GU- or U-rich sequence located downstream from the polyadenylation site and a highly conserved sequence of six nucleotides, namely AAUAAA, located 11-30 nucleotides upstream of the site. Termination and polyadenylation signals suitable for the present invention include those derived from SV40.

In addition to the embodiments already described, the expression vector of the present invention may also contain other specialized elements intended to increase the level of expression of cloned nucleic acids or to facilitate the identification of cells that carry the recombinant DNA. For example, a number of animal viruses contain DNA sequences that promote extra-chromosomal replication of the viral genome in permissive cell types. Plasmids bearing these viral replicons are replicated episomally as long as the appropriate factors are provided by genes either carried on the plasmid or with the genome of the host cell.

The expression vector of the present invention may or may not include a eukaryotic replicon. If a eukaryotic replicon is present, the vector is capable of amplification in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention may further comprise polynucleotide sequences that allow, for example, the translation of several proteins from a single mRNA, such as an internal ribosome entry site (IRES) and sequences for genomic integration of the promoter-chimeric polypeptide. Mammalian expression vectors are commercially available.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinarily skilled artisan and as such, no general description of selection considerations is provided herein.

Recombinant viral vectors are useful for in vivo expression of VDAC1 since they offer advantages such as lateral infection and targeting specificity of targeted cells.

Introduction of nucleic acids by viral infection offers several advantages over other methods such as lipofection and electroporation, since higher transfection efficiency can be obtained due to the infectious nature of viruses.

A recombinant cell of the present invention comprises a cell comprising a nucleic acid molecule that encodes a polypeptide or peptide of the invention. A variety of expression vector/host systems may be utilized to contain and express sequences encoding the viral antigens of the invention. These include, but are not limited to, microorganisms such as bacteria transformed with recombinant bacteriophages, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not meant to be limited by the host cell employed. The expression of the construct according to the present invention within the host cell may be transient or it may be stably integrated in the genome thereof.

VDAC1 Anti-apoptotic Activity and Human Disease

Mitochondria-mediated apoptosis may play a crucial role in aging and in the pathophysiology of many important diseases, including heart attack and stroke, neurodegenerative disorders such as Parkinson disease, Alzheimer disease, ALS and mitochondrial encephalomyopathies and cancer (Tatton and Olanow (1999). Biochim Biophys Acta 1410: 195-213; Olson and Kornbluth (2001). Curr Mol Med 1, 91-122). Moreover, in individual post-mortem brain regions of patients with Down syndrome, the level of VDAC1 is elevated whereas VDAC2 is normal, while in Alzheimer's disease, VDAC1 and/or VDAC2 are significantly reduced or elevated in the various brain regions (Olson and Kornbluth (2001). Curr Mol Med 1, 91-122). Some diseases, such as tumors, are caused by suppression of apoptosis, on the one hand, and other diseases, such as Alzheimer disease, are caused by increased apoptotic rate, on the other hand. Thus the anti-apoptotic activity of N-terminal truncated VDAC, and in particular of N-terminal truncated VDAC1 may be used for VDAC-based biologic therapy. Thus VDAC1 N-terminus may be an appropriate target for therapeutic agents designed to inhibit apoptosis.

Gene Therapy

It may be important to increase the expression of the nucleic acids of the invention in conditions requiring more augmented intercellular interactions for example, in neurodegenerative disorders, by means of gene therapy. Adenovirus (Adv)-mediated gene transfer has recently gained new attention as a means to deliver genes for cell or progenitor cell gene therapy. This is a rapidly growing field, both in terms of techniques and applications Pharmaceutical Compositions The present invention provides pharmaceutical compositions comprising a polypeptide, peptide or nucleic acid as described above and a physiologically acceptable carrier.

Depending on the location of the tissue of interest, a VDAC amino acid sequence can be supplied in any manner suitable for the provision of VDAC amino acid sequence. Thus, for example, a composition containing a source of VDAC amino acid sequence (i.e., a VDAC polypeptide or a VDAC expression vector, or cells expressing a VDAC amino acid sequence, as described herein) can be introduced into tissue of interest (e.g., injected, or pumped as a continuous infusion, or as a bolus within a tumor or intercutaneous or subcutaneous site, applied to all or a portion of the surface of the skin, dropped onto the surface of the eye, etc.).

Apart from other considerations, the fact that some of the novel active ingredients of the invention are polypeptides, peptides, peptide analogs or peptidomimetics, dictates that the formulation be suitable for delivery of these types of compounds. In general, peptides are less suitable for oral administration due to susceptibility to digestion by gastric acids or intestinal enzymes, but it is now disclosed that the compositions according to the present invention may be administered orally. The pharmaceutical composition of this invention may be administered by any suitable means, such as topically, or parenterally including intranasal, subcutaneous, intramuscular, intravenous, intra-arterial, intraarticular, or intralesional administration. Ordinarily, intravenous (i.v.), intraarticular or oral administration will be preferred.

The molecules of the present invention as active ingredients are dissolved, dispersed or admixed in a diluent or excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those in the art (see, for example, Ansel, Pharmaceutical Dosage Forms and Drug Delivery Systems. Malvern, Pa.: Williams and Wilkins, 1995; Gennaro (ed.), Remington's Pharmaceutical Sciences, 19th Edition (Mack Publishing Company 1995). In addition, if desired, the composition can contain minor amounts of auxiliary substances such as wetting or emulsifying agents, pH buffering agents.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example, polyethylene glycol, are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., (2001). Curr. Opin. Chem., Biol. 5, 447, 2001). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of a compound effective to prevent, delay, alleviate or ameliorate symptoms of a disease of the subject being treated. Determination of a therapeutically effective amount is well within the capability of those skilled in the art.

Toxicity and therapeutic efficacy of the polypeptides, fragments and analogs described herein can be determined by standard pharmaceutical procedures in cell cultures or experimental animals, e.g., by determining the 1050 (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (e.g. Fingl, et al., 1975, in "The Pharmacological Basis of Therapeutics", Ch. 1 p. 1, Laurence L. Brunton, Ed.).

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

In one particularly preferred embodiment according to the present invention, the peptides are administered orally (e.g. as a syrup, capsule, or tablet). In certain embodiments, peptide delivery can be enhanced by the use of protective excipients. This is typically accomplished either by complexing the peptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid based formulations for oral delivery of therapeutic agents).

Elevated serum half-life can be maintained by the use of sustained-release protein "packaging" systems. Such sustained release systems are well known to those of skill in the art. In one preferred embodiment, a biodegradable microsphere delivery system for proteins and peptides such as the ProLease® system (reviewed in Tracy (1998) Biotechnol Prog 14, 108-15) a dry powder composed of biodegradable polymeric microspheres containing the peptide in a polymer matrix that can be compounded as a dry formulation with or without other agents. Serum half-life can also be extended by conjugating the peptide or polypeptide of the invention to a moiety such as PEG using reagents and methods known to those with skill in the art.

The foregoing formulations and administration methods are intended to be illustrative and not limiting. It will be appreciated that, using the teaching provided herein, other suitable formulations and modes of administration can be readily devised.

A tablet may be made by compression or molding, optionally with one or more accessory ingredients. Compressed tablets may be prepared by compressing in a suitable machine the active peptide(s) in a free-flowing form such as a powder or granules, optionally mixed with a binder, (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface active or dispersing agent. Molded tablets may be made by molding in a suitable machine a mixture of the powdered peptide(s) moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile.

A syrup may be made by adding the active peptide(s) to a concentrated, aqueous solution of a sugar, for example, sucrose, to which may also be added any necessary ingredients. Such accessory ingredients may include flavorings, an agent to retard crystallization of the sugar or an agent to increase the solubility of any other ingredients, such as a polyhydric alcohol, for example, glycerol or sorbitol.

In addition to the aforementioned ingredients, the formulations of this invention may further include one or more accessory ingredient(s) selected from diluents, buffers, flavoring agents, binders, surface active agents, thickeners, lubricants, preservatives, (including antioxidants) and the like.

The proteins, peptides and nucleic acids of the present invention are to be administered in an amount effective in inhibiting apoptosis in the desired cells and to the desired duration.

It will be understood that the dosage may be an escalating dosage so that low dosage may be administered first, and subsequently higher dosages may be administered until an appropriate response is achieved. Also, the dosage of the composition can be administered to the subject in multiple administrations in the course of the treatment period in which a portion of the dosage is administered at each administration.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

In other embodiments the proteins or peptides of the present invention are delivered to cells as nucleic acids encoding the peptides in a non-viral gene delivery system. Particulate gene transfer systems are usually based on oligo- or polycationic carrier molecules which can condense nucleic acids by electrostatic interactions with their negatively charged phosphate backbone. The positive charge of cationic lipids leads to electrostatic interaction with the DNA, The lipidic moiety enables the hydrophobic collapse and the formation of so called 'lipoplexes'. Polycationic carrier molecules, like polylysine or polyethyleneimine (PEI) bind and condense DNA due to their high density of positive charges and result in the formation of so called 'polyplexes'. The surface of the delivery particle can be coated with hydrophilic polymers, e.g. polyethyleneglycol (PEG), which prevent binding to plasma proteins, blood cells and the RES and also enables a prolonged circulation time in the blood stream.

In yet another embodiment, the peptides of the present invention are delivered to cells in vesicles. Immunoliposomes have been described to allow targeted delivery of anticancer drugs into solid tumors (for review see Sapra and Allen (2004). Clin Cancer Res. 10(7), 2530-2537).

Polypeptides and peptides, and polynucleotide sequences of the present invention can be administered to a subject following microencapsulation. Methods of preparing microcapsules are known in the art and include preparation from an assortment of materials including natural and synthetic materials.

Delivery of Peptides and Proteins to the Brain

Overall, there are three types of recognized BBB transport systems:

Carrier-mediated transport (CMT); Active efflux transport (AET); and Receptor-mediated transport (RMT).

RMT systems have been used to bypass the BBB, in what has been termed the "Trojan horse" approach: one compound, which is recognized by the BBB as "friendly" and permitted to pass into the brain or actively transported into the brain (the "Trojan horse") is conjugated or fused to a therapeutic molecule. This technique is useful for delivery of therapeutic proteins into the brain for the treatment of, for example, lysosomal storage disorders (LSD) and neurodegenerative diseases.

The invention will now be illustrated by the following non-limiting examples.

EXAMPLES

Experimental Procedures

Plasmids and Site-Directed Mutagenesis

For construction of N-terminally truncated VDAC1, mVDAC1 cDNA was cloned into the BamHI and NotI restriction sites of the pcDNA4/TO vector (Invitrogen), using the following primers: CGGGATCCATGATAAAACTTGATTTGAAAACG (F) (SEQ ID NO:27) and GCGGCCGCTTATGCTTGAAATTCCAGTCC(R) (SEQ ID NO:28).

The G21W mutation was introduced using the restriction enzymes BamHI and XbaI and overlapping PCR using the following primers:

```
                                    (SEQ ID NO: 29)
GCGGATCCATGGCCGTGCCT (F), (SEQ ID NO: 30)
GCTCTAGATTATGCTTGAAATTCC (R), (SEQ ID NO: 31)
GGGATGTCTTCACCAAGTGGTACGG (F mutation), (SEQ ID NO: 32)
GCCGTACCACTTGGTTGAAGACATCC (R mutation).
```

The mutation sites are underlined. The mutated and truncated VDAC1 were cloned into pGEM-T Easy vector (Promega) for proliferation in *E. coli*. The mutations were confirmed by sequence analysis. The constructs were transferred into pcDNA4/To vector using BamHI and NotI/XbaI restriction sites. The mutated and truncated VDAC were expressed in T-REx-293 cells silenced for human VDAC1 expression by small hairpin (sh) RNA (Abu-Hamad et al. (2006). Proc. Natl. Acad. Sci. USA, 386, 73-83).

Apoptotic cell death was analyzed by Acridine Orange/Ethidium Bromide staining.

Cell Culture

T-REx-293 cells correspond to a transformed primary human embryonal kidney cell line, expressing the tetracycline repressor. hVDAC1-shRNA T-REx-293 cells stably expressing the pSUPERretro plasmid encoding shRNA targeting hVDAC1 were obtained and grown as described previously (Abu-Hamad et al. (2006), supra). The expression of hVDAC 1 in these cells is suppressed by 70-96% due to a gene silencing. hVDAC1-shRNA T-REx-293 cells expressing mVDAC1 or Δ(1-26)mVDAC1 were obtained by transfecting hVDAC1-shRNA-T-REx-293 cells with plasmid mVDAC1- or Δ(1-26)mVDAC1-pcDNA4/TO. Cells were grown with 200 μg/ml zeocin, 0.5 μg/ml puromycin and 5 μg/ml blasticidine, with mVDAC1 or Δ(1-26)mVDAC1 expression under tetracycline control. Cell viability was analyzed by staining with acridine orange and ethidium bromide in PBS (Zaid et al. (2005). Cell death and differentiation, 12, 751-760). Images were recorded using Zeiss LSM510 confocal or Olympus IX51 fluorescence microscopes. Mitochondria preparation and measurements of ATP levels and $Ca^+$ accumulation were carried out as previously described (Abu-Hamad et al. (2006), supra).

Yeast Strains, Cultivation Conditions and VDAC Expression:

The expression of native and mutated murine VDAC1 was conducted in the *Saccharomyces cerevisiae* por1-mutant strain M22-2 (MATa, lys2 his4 trp1 ade2 ura3) under the control of the yeast porin1 (YVDAC1) promoter in a low-copy number plasmid (pSEYC58). *S. cerevisiae* M22-2 and its evolved mutant were cultured at 30° C. in selective minimal medium containing ammonium sulfate, yeast nitrogen base, the required amino acids and 2% glucose or in rich medium containing 1% yeast extract, 2% peptone (YP) with 2% lactate (YPL) or glucose (YPD) at pH 5.5. For VDAC purification, mitochondria were isolated from yeast cultured in lactate containing rich medium (to induce mitochondria biogenesis).

Purification of VDAC:

Native and mutated mVDAC1 were extracted with LDAO from mitochondria isolated from yeast expressing native or mutated mVDAC, and purified by chromatography on hydroxyapatite followed by carboxymethyl (CM)-cellulose where LDAO was replaced by β-OG (Shoshan-Barmatz and Gincel (2003), supra).

Cytochrome c Release Induced by Staurosporine (STS):

hVDAC1-shRNA T-REx-293 cells stably expressing native or Δ(1-26)mVDAC1 were grown on 60 mm plates. Native or truncated mVDAC1 expression was triggered by tetracycline (1 μg/ml). Seventy-two hours later, cells were exposed to STS (1.25 μM) for 5 h. Cells were harvested, washed twice with PBS, incubated on ice for 1 h in extraction buffer (200 mM manitol, 70 mM sucrose, 1 mM EGTA, 1 mM EDTA, 10 μg/ml leupeptine, 1 mM PMSF, 1 mg/ml BSA, 10 mM HEPES, pH 7.5) and then lysed with a Dounce homogenizer by 25 strokes. Homogenates were centrifuged (1000× g) at 4° C. for 10 min and the supernatants were re-centrifuged at 15,000×g for 30 min at 4° C. Aliquots (10 μl) of the resultant supernatants, designated as the cytosolic fraction, were immediately boiled in SDS-PAGE sample buffer and resolved by SDS-PAGE on Tris-Tricine gels (13% polyacrylamide) and immunoblotted using monoclonal anti-cytochrome c antibodies. To rule out mitochondrial contamination of the cytosolic fraction, the presence of VDAC was tested by immunoblotting. Although supernatants from the different treated cultures were derived from equal number of cells, protein concentration in the total cells lysates were estimated as well as, actin levels were analyzed by immunoblotting using anti-actin antibodies.

Single Channel Recording and Analysis:

Reconstitution of purified native or Δ(1-26)mVDAC1 into planar lipid bilayers (PLB), channel recording and analysis were carried out as previously described (Gincel et al. (2001). Biochem J 358 (Pt 1), 147-155). Briefly, PLB were prepared from soybean asolectin dissolved in n-decane (50 mg/ml) in a chamber containing 10 mM Hepes/KOH, pH 7.4 and 0.5 or 1M NaCl (cis/trans). Only PLBs with a resistance greater than 100 GΩ were used. Purified VDAC (about 1 ng) was added to the chamber defined as the cis side. After insertion of one or more channels into the PLB, excess protein was removed by perfusion of the cis chamber with 20 volumes of a same solution. Currents were recorded under voltage-clamp mode using a Bilayer Clamp amplifier (Warner Instruments, Hamden, Conn.). Currents were measured with respect to the trans side of the membrane (ground). The currents were low-pass filtered at 1 kHz, using a Bessal filter (Frequency Devices, Haverhill, Mass.) and digitized on-line using a Digidata 1200 interface board and pCLAMP 6 software (Axon Instruments). Sigma Plot 2000 scientific software was used for data analyses. Experiments were performed at 23-25° C.

Real Time Surface Plasmon Resonance:

Surface plasmon resonance (SPR) using the ProteOn-XPR36 (Bio-Rad, USA) system was employed to study the interaction of VDAC1 N-terminal peptides with purified HK-I and Bcl2. Purified rat brain HK-I, recombinant Bcl2 and rabbit IgG were immobilized on a CM5 sensor surface according to the manufacture's instructions. N-terminal VDAC1 peptides were diluted in running buffer (150 mM NaCl, 0.005% Tween-20, 4% (V/V) DMSO, 10 mM PBS, pH, 7.4) and injected onto the sensor chip at varying concentrations at a flow rate of 40 µl/min at 25° C.

Results

Example 1

Effect of N-Terminal Truncated VDAC Protein on Cell Growth

RNA interference (RNAi), a post-transcriptional, highly conserved process in eukaryotes that leads to specific gene silencing through degradation of the target mRNA has been used as a tool to control the expression of specific genes in numerous organisms. The expression of endogenous VDAC1 in transformed primary human embryonal kidney T-REx-293 cells was suppressed using a single shRNA targeting a coding region of human VDAC1 as described hereinabove.

VDAC protein provides the major pathway for nucleotides, $Ca^{2+}$ and other metabolites moving across the outer mitochondrial membrane (OMM). To verify the requirement of the N-terminal region for the transport activity of VDAC1, N-terminally truncated mVDAC1 was expressed in human embryonal kidney T-REx-293 cells suppressed for human VDAC1 expression by ~85% using a single hVDAC1-shRNA. Such cells proliferated slowly as compared to normal cells (FIG. 2A) due to low levels of ATP and ADP and a reduced ATP synthesis capacity, all of which could be restored by expression of mVDAC1 under the control of tetracycline. Expression of N-terminal truncated mouse VDAC ($\Delta$(1-26)mVDAC1) in cells silenced for hVDAC1 restored cell growth (FIG. 2A), suggesting that the 26 residues N-terminal are not essential for VDAC1 function in cell growth.

Figure 3:
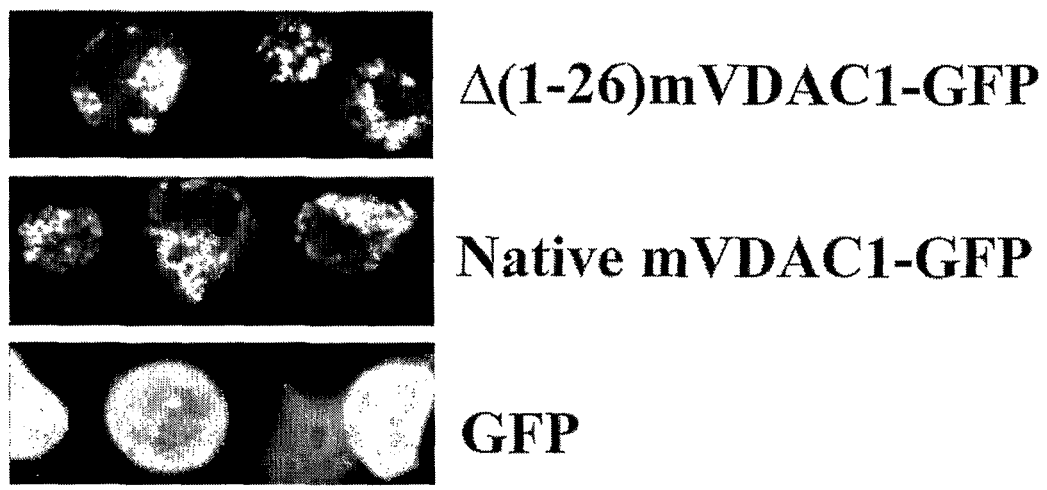
FIG. 3 shows a comparison of the distribution of N-terminal truncated- and native mVDAC1 expressed in hVDAC1-shRNA-T-REx-293 transiently transfected with either native or Δ1-26 mVDAC1 as revealed by confocal microscopy (scale bars: 20 μm).

Localization of the native and N-terminal truncated VDAC1 was examined by confocal images of hVDAC1-shRNA cells expressing mVDAC1-GFP or $\Delta$(1-26)mVDAC1-GFP or GFP alone. While cells expressing GFP showed diffuse green fluorescence, cells expressing mVDAC1-GFP or truncated mVDAC1-GFP showed similarly distributed punctuated fluorescence confined to membranes, suggesting that both native and truncated mVDAC1 were both localized to mitochondria (FIG. 3).

Figure 4:
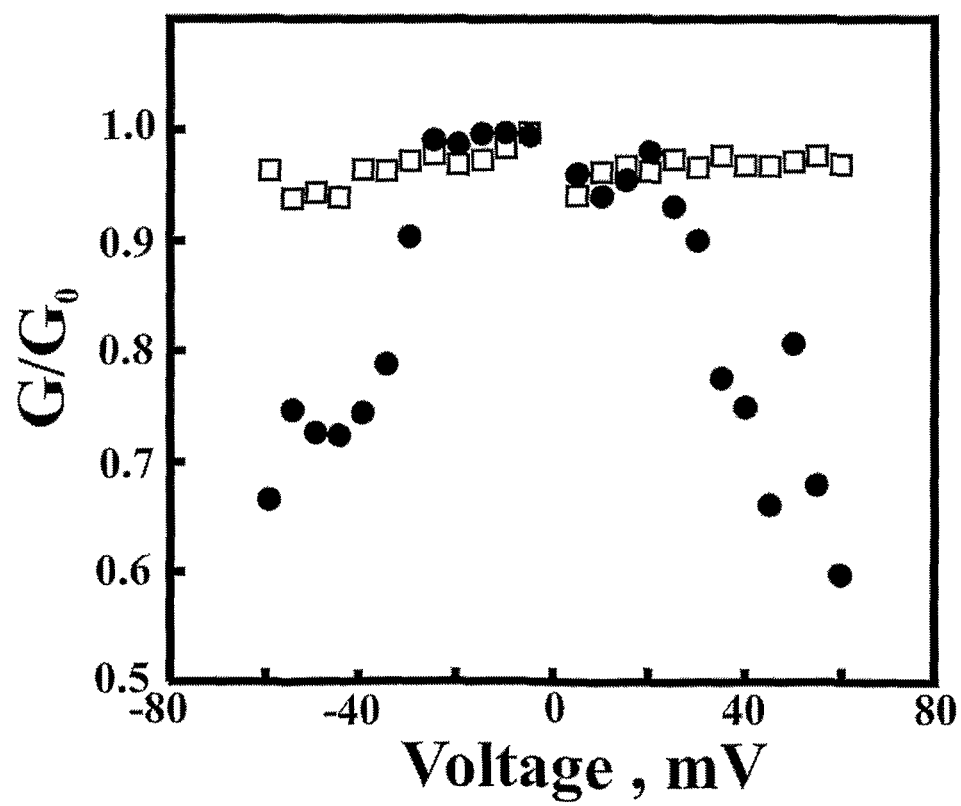
FIG. 4 shows relative conductance of native mVDAC1 and truncated Δ(1-26)mVDAC1 reconstituted into a planar lipid bilayer (PLB). Relative conductance was determined as the ratio of conductance at a given voltage (G) to the maximal conductance (Go). The experiments are representative of 4 similar experiments.

The activity of $\Delta$(1-26)mVDAC1 was also analyzed following its reconstitution into a planar lipid bilayer. A maximal conductance of 4 nS (at 1M NaCl) was obtained for both native and N-terminally truncated protein. However, whereas bilayer reconstituted-mVDAC1 displayed typical voltage-dependence conductance, highest at transmembrane potentials close to zero and decreasing at both high negative and positive potentials (FIG. 4), $\Delta$(1-26)mVDAC1 by contrast, showed no voltage dependence and exhibited high conductance at all tested voltages (FIG. 4). Since there is no significant membrane potential across the OMM, the loss of voltage sensitivity of the $\Delta$(1-26)mVDAC1 may has no physiological significance, as also reflected in its cellular activity similar to that of the voltage sensitive intact protein.

The results thus show that N-terminally truncated VDAC1 is as functional as the native protein as reflected in its ability to restore cell growth, and in the channel conductance capacity of the purified proteins, all of which are compatible to the native protein. Therefore, the N-terminal α-helix of VDAC1 is not required for cell growth, VDAC1 transport activity or mitochondrial energy production.

Example 2

Cells Expressing N-Terminal-Truncated mVDAC1 do not Release Cytochrome c and are Resistant to Apoptosis The ability to suppress endogenous hVDAC1 expression in T-REx-293 and to introduce native and mutated mVDAC1 was used to further explore the involvement of VDAC1 in apoptosis.

Figure 5:
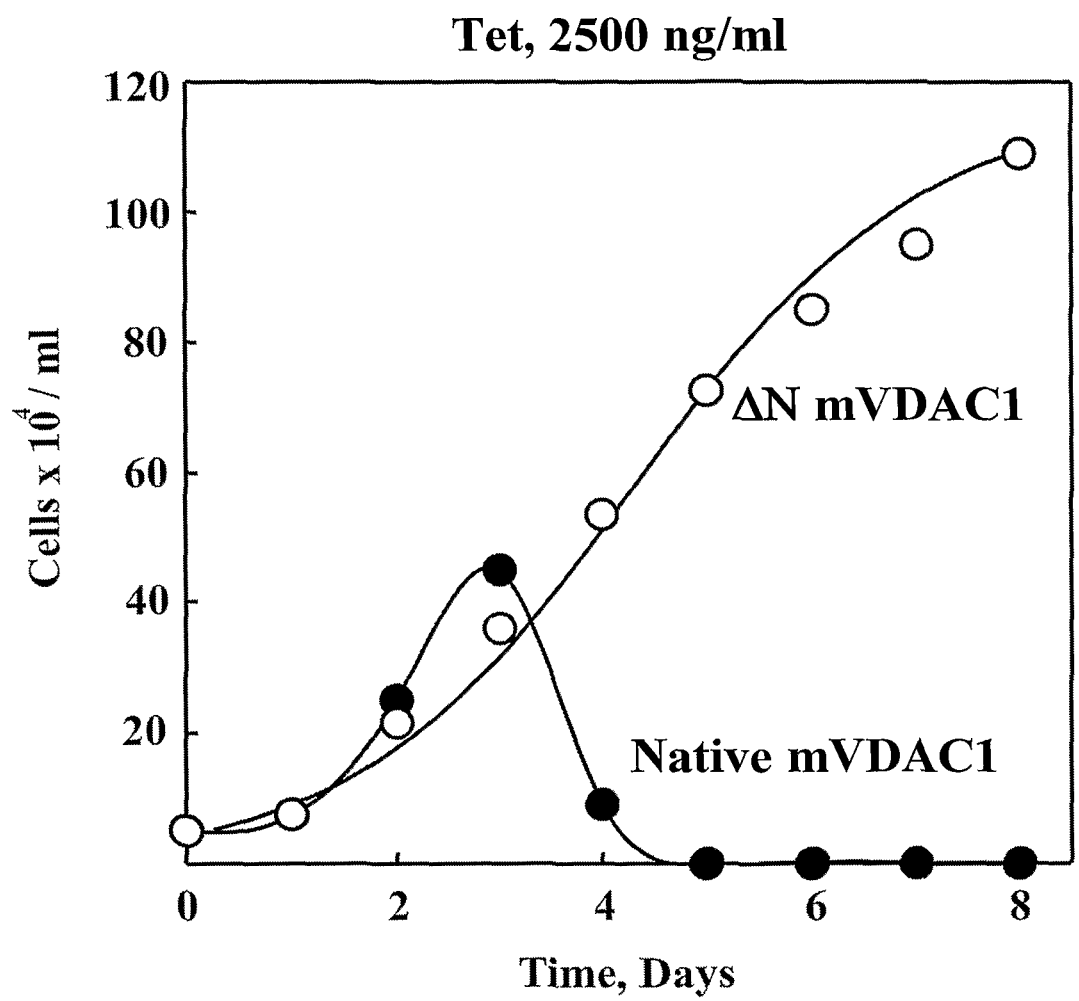
FIG. 5 illustrates that overexpression of native mVDAC1 but not truncated A 1-26 mVDAC1 triggers cell death. In T-REx-293 cells silenced for hVDAC1 expression, over-expression of native mVDAC1 induced by 2.5 μg/ml tetracycline triggered cell death on day 4 (●). Under the same conditions, cells over-expressing N-terminal truncated mVDAC1 showed no cell death even after day 8 (○). Data, analyzed by ANOVA and t test, show the mean±S.E.M. (n=3).

Native and truncated mVDAC1 expression was induced by low (1.0 µg/ml) or high (2.5 µg/ml) tetracycline (Tet) in T-REx-293 cells silenced for hVDAC1 expression. As is shown in FIG. 5, over-expression of native VDAC1 induced by 2.5 µg/ml tetracycline, triggered cell death on day 4 and complete cell death by day 5. Under the same conditions, cells expressing truncated $\Delta$1-26 mVDAC1 continue to grow over 8 days, with only 5-8% apoptotic cell death. These results indicate that cells expressing N-terminally truncated VDAC1 lost the ability to undergo mitochondria-mediated apoptotic cell death.

Figure 6:
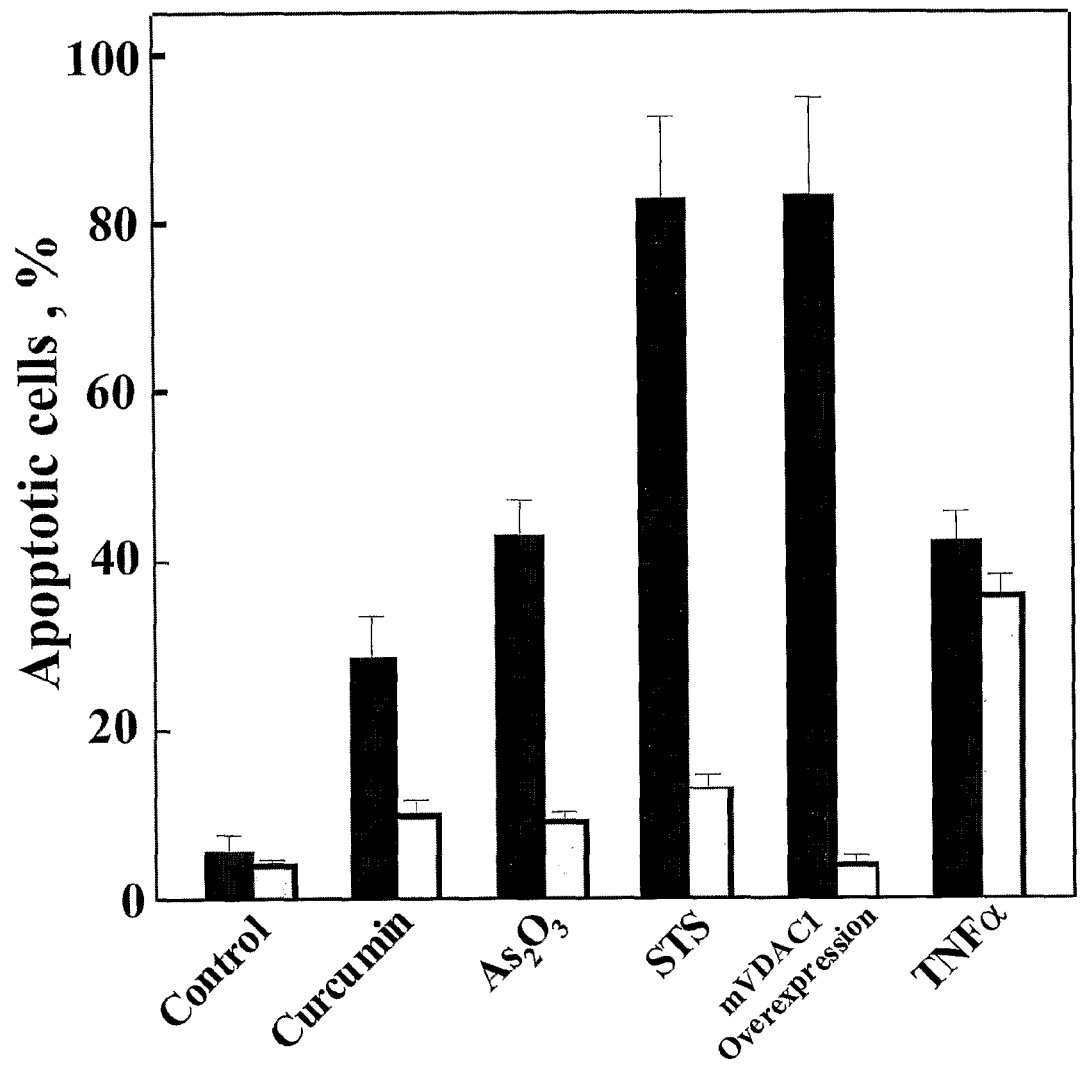
FIG. 6 shows that cells expressing truncated Δ1-26 mVDAC1 are resistance to apoptosis induction. T-REx-293 cells silenced for hVDAC1 and expressing N-truncated mVDAC1 (grey columns) were resistant to apoptosis induced by curcumin (100 μM), $As_2O_3$ (60 μM) or STS (1.25 μM), while cells expressing native mVDAC1 (black columns) were sensitive to those stimuli. Overexpression, as induced by tetracycline (2.5 μg/ml), of mVDAC1 but not Δ(1-26)mVDAC1 undergo apoptosis. Both cell lines showed similar sensitivity to apoptosis induced by TNFα (25 ng/ml). Quantitative analysis of apoptosis in the different cell types was performed by ANOVA and t test; p<0.001 (***) was considered statistically significant. Data shown represent the mean±S.E.M. (n=4).

The involvement of the N-terminal region of VDAC1 in mediating apoptosis as induced by various stimuli was next tested. hVDAC1-shRNA-T-REx-293 cells expressing mVDAC1 or $\Delta$(1-26)mVDAC1 were challenged with various apoptosis-inducing agents each acting via a different mechanism yet all involving mitochondria (FIG. 6). Staurosporine (STS) (Zaid et al. (2005), supra), curcumin (Bae et al. (2003). Biochem Biophys Res Commun 303 (4), 1073-1075) and $As_2O_3$ (Zheng et al. (2004). Oncogene 23 (6), 1239-1247) all induced death in cells expressing native mVDAC1 but not in those expressing $\Delta$(1-26)mVDAC1. By contrast, TNFα, an agent that activates apoptosis via a mitochondria-independent pathway, induced a similar extent of cell death in native- and $\Delta$(1-26)-mVDAC1-expressing cells. It seems, therefore, that the VDAC1 N-terminal region is necessary for apoptosis to take place.

Figure 7:
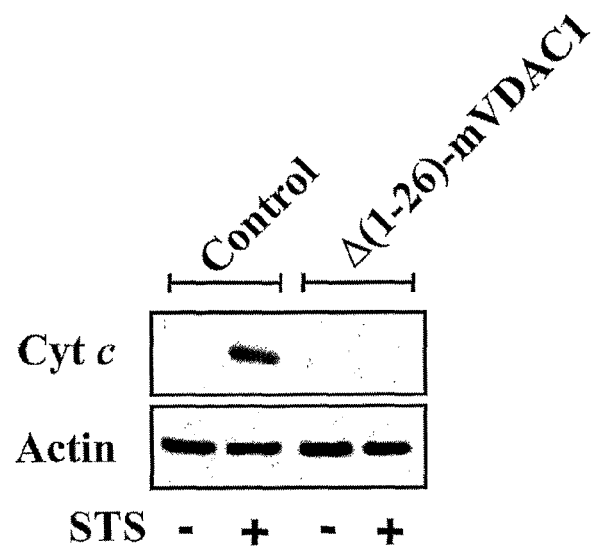
FIG. 7 illustrates that no cytochrome c was released in cells expressing N-terminal truncated VDAC1. T-REx-293 or hVDAC1-shRNA-T-REx-293 cells expressing mVDAC1 or Δ(1-26) mVDAC1, as induced by tetracycline (1 μg/ml), were exposed to STS (1.25 μM) for 5 h and cytochrome c released into the cytosol was assayed using anti-cytochrome c antibodies.

While cell death induced by the various reagents tested above is mediated by different pathways, all ultimately lead to cytochrome c release, a main step is cell apoptosis. To verify whether the apoptotic resistance of $\Delta$(1-26)mVDAC1-expressing cells is due to an inability of the cells to release cytochrome c, cells expressing native mVDAC1 or $\Delta$(1-26) mVDAC1 were exposed to STS and the extent of cytochrome c release into the cytosol was analyzed. Western blotting using anti-cytochrome c monoclonal antibodies showed that cytochrome c was released to the cytosol of cells expressing native mVDAC1 but not from cells expressing $\Delta$(1-26)mVDAC1 (FIG. 7). The finding that no cytochrome c release is elicited by STS in $\Delta$(1-26)mVDAC1-expressing cells clearly shows that the N-terminal region of VDAC1 is essential for cytochrome c release.

Example 3

N-Terminal GXXXG Mutated VDAC

In order to verify whether the GXXXG motif is involved in VDAC apoptotic activity, possibly via oligomerization, the glycine (Gly) at position 21 in the GXXXG motif is replaced by tryptophan (Trp). The mutated protein will be analyzed, Disruption of VDAC oligomerization due to mutations in GXXXG, but not by mutations in other positions, will provides an indication of the specificity and importance of this motif in VDAC oligomerization. Interestingly, upon purification of large amount of VDAC for crystallization study, the co-purification with VDAC of an anti-VDAC antibody non-reacting 72 kDa protein was observed (FIG. 10). MALDI-TOF analysis of this protein band identified it as VDAC1. Since the anti-VDAC antibody recognizes specifically the N-terminal of VDAC (Babel, D. et al., (1991) Biol. Chem. Hoppe Seyler. 372, 1027-1034), the results suggest that the N-terminal is not exposed to the antibody recognizing the N-terminal and thus it is most likely that the N-terminal is involved in the VDAC dimer formation.

Example 4

N-Terminal VDAC1 Peptide as a Target for Drugs, Peptides, Proteins

Figure 8:
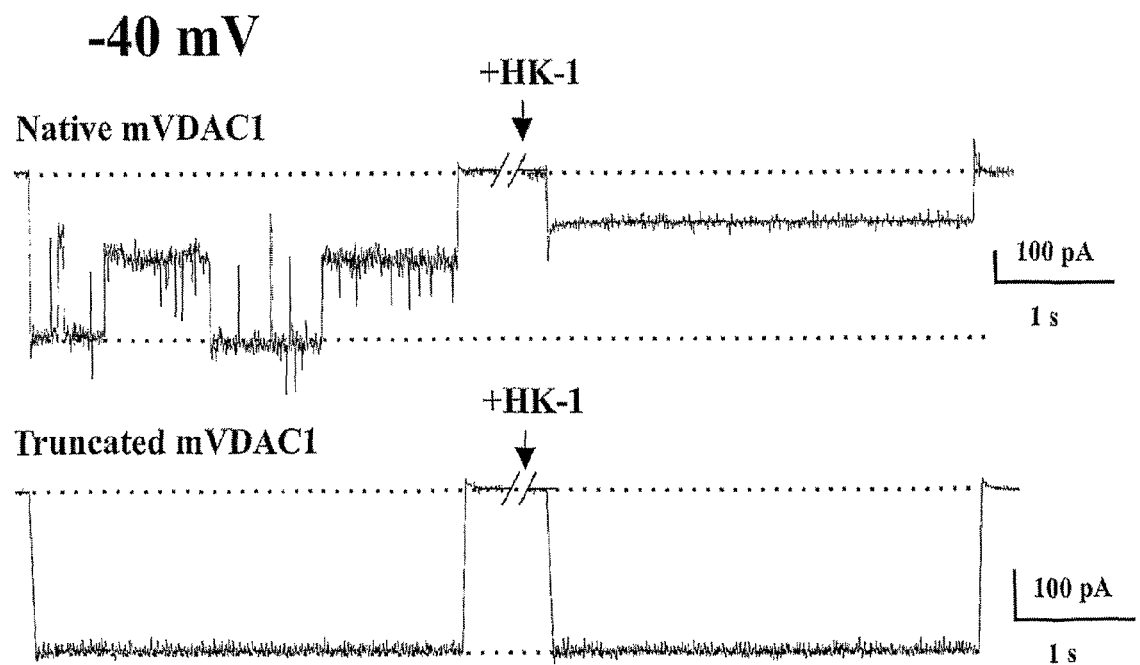
FIG. 8 shows that HK-I and Bcl2 binds to mVDAC1 but not to N-terminus truncated protein and modified its channel activity. Purified HK-I and Bcl2 interaction with bilayer reconstituted native and Δ1-26-mVDAC1 was monitored. Currents through bilayer-reconstituted mVDAC1 or Δ(1-26) mVDAC1 in response to a voltage step from 0 to +40 mV were recorded before and 10 min after the addition of HK-I (28 mU/ml) (FIG. 8). The dashed lines indicate the zero and the maximal current levels.

The interaction of the VDAC1 N-terminal region with purified rat brain HK-I and Bcl2 was demonstrated using bilayer-reconstituted VDAC1 and surface plasmon resonance (SPR) technology. Native and Δ(1-26)mVDAC1 were expressed in porin-less yeast, purified and reconstituted into planar lipid bilayers. As demonstrated previously (Azoulay-Zohar et al. (2004) Biochemical J. 377, 347-355), addition of HK-I to bilayer-reconstituted native VDAC1 induced the channel to fluctuate between the fully open, sub-conducting state to a stable, long-lived low-conducting state (FIG. 8). As would be expected for a voltage-insensitive channel (FIG. 4), Δ(1-26) mVDAC1 assumed a stable high-conducting open conformation. HK-I had no effect on channel activity of the truncated version of VDAC1, suggesting that HK-I interacts with the VDAC1 N-terminal region. These results thus indicate that the VDAC1 N-terminal region is required for interaction with anti-apoptotic proteins, for example HK-I.

Figure 9A:
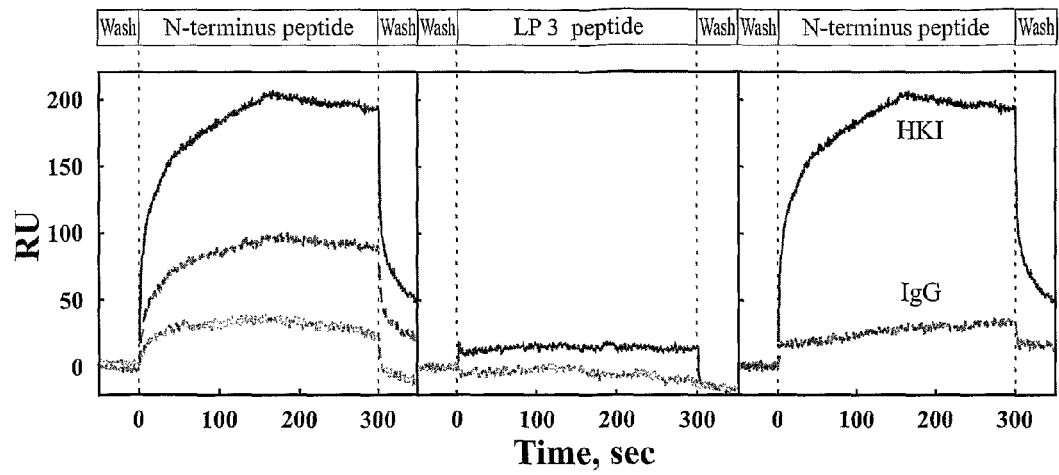
FIG. 9 illustrates the binding of VDAC1-N-terminus peptide to HK-I (FIG. 9A) or Bcl2 (FIG. 9B). Using the microfluid-array format of the ProteOn and the SPR technology, five different concentrations of the peptides VDAC1-N-terminus, or VDAC1 internal loop (LP3) were run in parallel over surface-strip of the HK-1-Dextran, Bcl2-Dextran or γ-gluboline (IgG)-Dextran (as control). Responses (resonance units, RU) as a function of peptide concentration were monitored using the ProteOn imaging system and related Soft-Wear-tools.
Figure 9B:
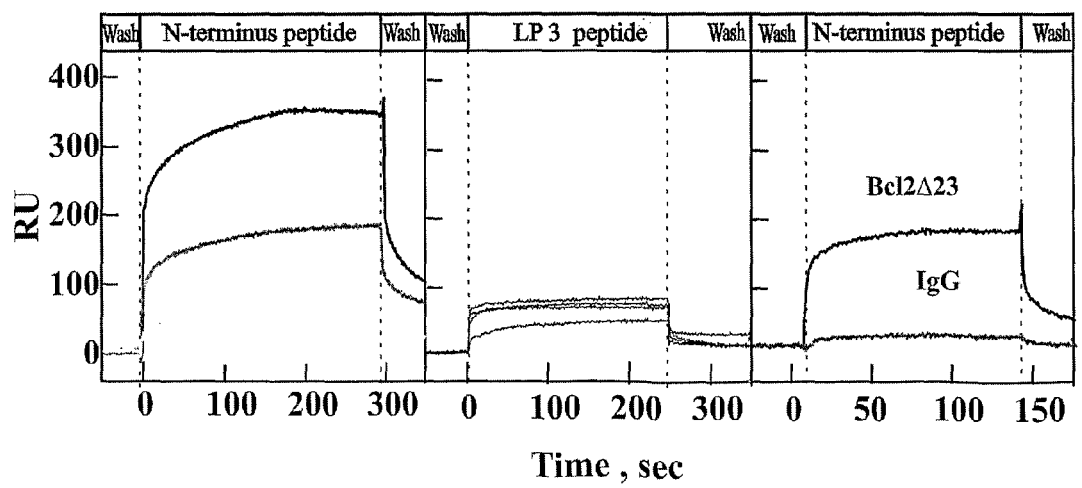

To further assess the interaction of the VDAC1 N-terminal region with HK-I and Bcl2, purified HK-I, recombinant Bcl2 or rabbit IgG were coupled to an SPR biosensor chip. Increasing concentrations of a peptide corresponding to the N-terminal region of VDAC1 were then injected onto the sensor chips and binding HK-I or Bcl2 was measured. The N-terminal peptide strongly bound to immobilized HK-I (FIG. 9A) or Bcl2 (FIG. 9B) in a concentration- and time-dependent manner, rapidly associated with and dissociated from the immobilized proteins. The binding of the VDAC1 N-terminal peptide to HK-I and Bcl2 was specific, since no signal was obtained with the IgG-immobilized chip. Moreover, another VDAC1-based peptide, representing a loop (LP3; E157 to T174, 18 amino acids) predicted to face the intermembranal space, did not interact with either HK-I (FIG. 9A) or Bcl2 (FIG. 9B). The results demonstrate direct interaction of the VDAC1 N-terminal peptide with HK-I and Bcl2. Thus, it can be used as a target for drugs, peptides, proteins etc., interfering with its function in apoptosis.

Example 5

Figure 12:
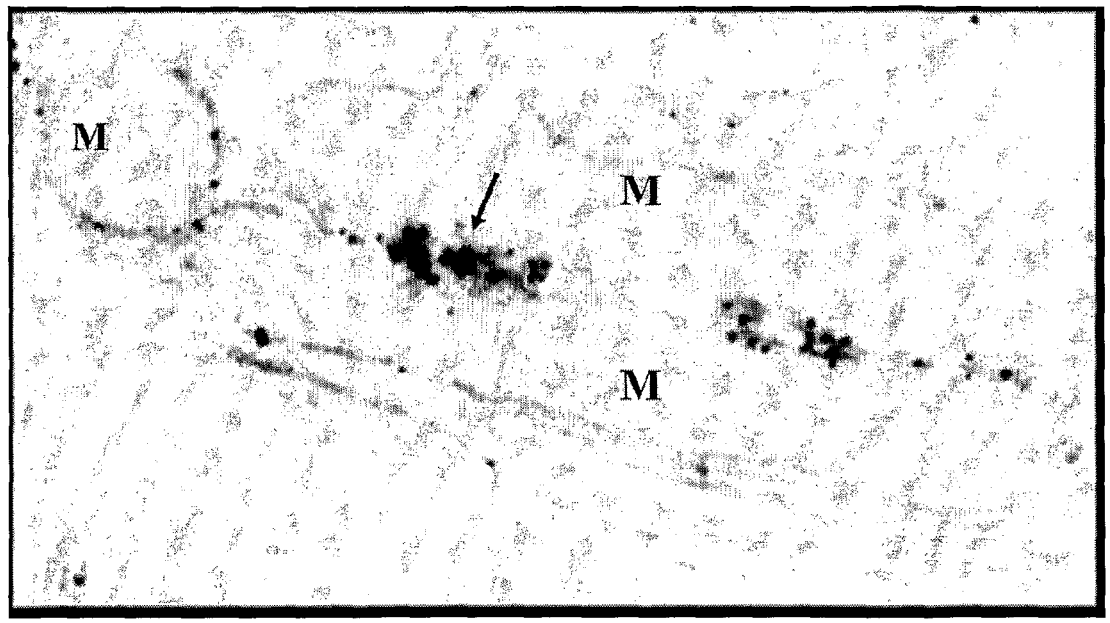
FIG. 12 shows Electron micrograph of mitochondria in the molecular layer immunostained with anti-VDAC antibodies. Stain is localized to mitochondrial outer membrane (arrows) with tendency to concentrate at contact region between mitochondria (arrowheads). m, mitochondrion. The immunostaining with anti-VDAC N-terminal indicates that the N-terminal is exposed and not imbedded in the membrane).

Part of the VDAC1 N-Terminus is Exposed to Specific Anti-VDAC N-Terminal Antibody Immunohistochemical staining of VDAC in rat cerebellum showed high labeling of the Purkinje neurons (Shoshan-Barmatz et al, 2004, Biochem. Biophys. Acta 1657, 105-114). Immunogold labeling and EM analysis of the cerebellar molecular layer showed specific VDAC immunostaining of the mitochondrial outer membrane, highly enhanced in contact sites between mitochondria (FIG. 12). The immunostaining with anti-VDAC N-terminal specific antibody indicates that the N-terminal is exposed to the cytosol The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. An isolated N-terminal voltage-dependent anion channel (VDAC) variant molecule capable of inhibiting apoptosis in a cell, the VDAC variant molecule selected from the group consisting of an isolated N-terminal domain mutated VDAC polypeptide and an isolated N-terminal domain mutated VDAC derived polypeptide of up to 70 amino acids, wherein the N-terminal domain of the isolated polypeptides comprise amino acids 1-26 of the VDAC polypeptide, wherein the mutation is a point mutation within a GXXXG amino acid sequence located within said N-terminal domain.

2. The isolated VDAC variant molecule according to claim 1, wherein the VDAC is selected from a VDAC1 isomer, VDAC2 isomer and VDAC3 isomer.

3. The isolated N-terminal mutated VDAC polypeptide according to claim 1 wherein the point mutation is a substitution of glycine at position 21 to tryptophan to provide a polypeptide having the amino acid sequence as set forth in SEQ ID NO:33.

4. The isolated N-terminal mutated VDAC derived polypeptide according to claim 1 wherein the mutation is a substitution of glycine at position 21 to tryptophan to provide a polypeptide having the amino acid sequence as set forth in SEQ ID NO:36.

5. An isolated polynucleotide encoding a VDAC variant molecule selected from an N-terminal domain mutated VDAC polypeptide and an N-terminal domain mutated VDAC derived polypeptide according to claim 1.

6. A polynucleotide construct comprising the isolated polynucleotide according to claim 5.

7. The polynucleotide construct according to claim 6, wherein the construct comprises an expression vector.

8. A host cell comprising a construct according to claim 7.

9. A pharmaceutical composition comprising an isolated N-terminal voltage-dependent anion channel (VDAC) variant molecule according to claim 1.

10. The pharmaceutical composition according to claim 9 comprising an isolated N-terminal domain mutated VDAC polypeptide having the amino acid sequence as set forth in SEQ ID NO:33.

11. The pharmaceutical composition according to claim 9 comprising an isolated N-terminal domain mutated VDAC derived polypeptide having an amino acid sequence as set forth in SEQ ID NO:36.

12. The pharmaceutical composition of claim 9 further comprising a pharmaceutically acceptable carrier or excipient.

13. A method for inhibiting apoptosis in a cell comprising the step of administering to the cell a molecule according to claim 1, said cell is under conditions sufficient to inhibit apoptosis of the cell.

14. A method for inhibiting apoptosis in a cell comprising the step of administering to the cell a polynucleotide according to claim 5, said cell is under conditions sufficient to inhibit apoptosis of the cell.

* * * * *

SEQUENCE LISTING

```
<160> NUMBER OF SEQ ID NOS: 36

<210> SEQ ID NO 1
<211> LENGTH: 257
<212> TYPE: PRT
<213> ORGANISM: Artificial Sequence
<220> FEATURE:
<223> OTHER INFORMATION: SYNTHETIC PEPTIDE

<400> SEQUENCE: 1

Ile Lys Leu Asp Leu Lys Thr Lys Ser Glu Asn Gly Leu Glu Phe Thr
1               5                   10                  15

Ser Ser Gly Ser Ala Asn Thr Glu Thr Thr Lys Val Thr Gly Ser Leu
            20                  25                  30

Glu Thr Lys Tyr Arg Trp Thr Glu Tyr Gly Leu Thr Phe Thr Glu Lys
        35                  40                  45

Trp Asn Thr Asp Asn Thr Leu Gly Thr Glu Ile Thr Val Glu Asp Gln
    50                  55                  60
```

```
Leu Ala Arg Gly Leu Lys Leu Thr Phe Asp Ser Ser Phe Ser Pro Asn
 65                  70                  75                  80

Thr Gly Lys Lys Asn Ala Lys Ile Lys Thr Gly Tyr Lys Arg Glu His
                 85                  90                  95

Ile Asn Leu Gly Cys Asp Met Asp Phe Asp Ile Ala Gly Pro Ser Ile
            100                 105                 110

Arg Gly Ala Leu Val Leu Gly Tyr Glu Gly Trp Leu Ala Gly Tyr Gln
        115                 120                 125

Met Asn Phe Glu Thr Ala Lys Ser Arg Val Thr Gln Ser Asn Phe Ala
    130                 135                 140

Val Gly Tyr Lys Thr Asp Glu Phe Gln Leu His Thr Asn Val Asn Asp
145                 150                 155                 160

Gly Thr Glu Phe Gly Gly Ser Ile Tyr Gln Lys Val Asn Lys Lys Leu
                165                 170                 175

Glu Thr Ala Val Asn Leu Ala Trp Thr Ala Gly Asn Ser Asn Thr Arg
            180                 185                 190

Phe Gly Ile Ala Ala Lys Tyr Gln Ile Asp Pro Asp Ala Cys Phe Ser
        195                 200                 205

Ala Lys Val Asn Asn Ser Ser Leu Ile Gly Leu Gly Tyr Thr Gln Thr
    210                 215                 220

Leu Lys Pro Gly Ile Lys Leu Thr Leu Ser Ala Leu Leu Asp Gly Lys
225                 230                 235                 240

Asn Val Asn Ala Gly Gly His Lys Leu Gly Leu Gly Leu Glu Phe Gln
                245                 250                 255

Ala

<210> SEQ ID NO 2
<211> LENGTH: 774
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 2
ataaagcttg atttgaaaac aaaatctgag aatggattgg aatttacaag ctcaggctca      60
gccaacactg agaccaccaa agtgacgggc agtctggaaa ccaagtacag atggactgag     120
tacggcctga cgtttacaga gaatggaat accgacaata cactaggcac cgagattact      180
gtggaagatc agcttgcacg tggactgaag ctgaccttcg attcatcctt ctcacctaac     240
actgggaaaa aaaatgctaa atcaagaca gggtacaagc gggagcacat taacctgggc      300
tgcgacatgg atttcgacat tgctgggcct tccatccggg gtgctctggt gctaggttac     360
gagggctggc tggccggcta ccagatgaat tttgagactg caaaatcccg agtgacccag     420
agcaactttg cagttggcta caagactgat gaattccagc ttcacactaa tgtgaatgac     480
gggacagagt ttggcggctc catttaccag aaagtgaaca agaagttgga gaccgctgtc     540
aatcttgcct ggacagcagg aaacagtaac acgcgcttcg gaatagcagc caagtatcag     600
attgaccctg acgcctgctt ctcggctaaa gtgaacaact ccagcctgat aggtttagga     660
tacactcaga ctctaaagcc aggtattaaa ctgacactgt cagctcttct ggatggcaag     720
aacgtcaatg ctggtggcca caagcttggt ctaggactgg aatttcaagc ataa           774

<210> SEQ ID NO 3
<211> LENGTH: 257
<212> TYPE: PRT
```

<213> ORGANISM: Artificial Sequence
<220> FEATURE:
<223> OTHER INFORMATION: SYNTHETIC PEPTIDE

<400> SEQUENCE: 3

Ile Lys Leu Asp Leu Lys Thr Lys Ser Glu Asn Gly Leu Glu Phe Thr
1               5                   10                  15
Ser Ser Gly Ser Ala Asn Thr Glu Thr Thr Lys Val Asn Gly Ser Leu
            20                  25                  30
Glu Thr Lys Tyr Arg Trp Thr Glu Tyr Gly Leu Thr Phe Thr Glu Lys
        35                  40                  45
Trp Asn Thr Asp Asn Thr Leu Gly Thr Glu Ile Thr Val Glu Asp Gln
50                  55                  60
Leu Ala Arg Gly Leu Lys Leu Thr Phe Asp Ser Ser Phe Ser Pro Asn
65                  70                  75                  80
Thr Gly Lys Lys Asn Ala Lys Ile Lys Thr Gly Tyr Lys Arg Glu His
                85                  90                  95
Ile Asn Leu Gly Cys Asp Val Asp Phe Asp Ile Ala Gly Pro Ser Ile
            100                 105                 110
Arg Gly Ala Leu Val Leu Gly Tyr Glu Gly Trp Leu Ala Gly Tyr Gln
        115                 120                 125
Met Asn Phe Glu Thr Ser Lys Ser Arg Val Thr Gln Ser Asn Phe Ala
130                 135                 140
Val Gly Tyr Lys Thr Asp Glu Phe Gln Leu His Thr Asn Val Asn Asp
145                 150                 155                 160
Gly Thr Glu Phe Gly Gly Ser Ile Tyr Gln Lys Val Asn Lys Lys Leu
                165                 170                 175
Glu Thr Ala Val Asn Leu Ala Trp Thr Ala Gly Asn Ser Asn Thr Arg
            180                 185                 190
Phe Gly Ile Ala Ala Lys Tyr Gln Val Asp Pro Asp Ala Cys Phe Ser
        195                 200                 205
Ala Lys Val Asn Asn Ser Ser Leu Ile Gly Leu Gly Tyr Thr Gln Thr
210                 215                 220
Leu Lys Pro Gly Ile Lys Leu Thr Leu Ser Ala Leu Leu Asp Gly Lys
225                 230                 235                 240
Asn Val Asn Ala Gly Gly His Lys Leu Gly Leu Gly Leu Glu Phe Gln
                245                 250                 255
Ala

<210> SEQ ID NO 4
<211> LENGTH: 774
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 4
ataaaacttg atttgaaaac gaagtcagag aatggattgg aatttaccag ctcaggctct      60
gccaacacgg aaaccaccaa agtgaacggc agcctggaaa ccaagtacag atggactgag     120
tatgggctga cgtttacaga gaagtggaac acagacaaca ccctgggcac tgagatcact     180
gtggaagacc agcttgctcg tggactgaag ctcacctttg attcgtcatt ctcgccgaac     240
actgggaaaa aaaatgctaa aatcaagaca gggtacaaga gggagcacat caacctcggc     300
tgtgacgtgg actttgacat cgctgggccc tcgatccggg gcgctctggt gcttggctat     360
gagggttggc tggctggcta ccagatgaat tttgagacct cgaagtcccg agtgacccag     420

```
agcaacttcg cagttggcta taagacggat gaattccagc ttcatactaa tgtgaatgac    480
gggacagagt ttggtggctc catttaccag aaggtgaaca agaagttgga gactgctgtc    540
aatctcgcct ggactgcagg aaacagtaac actcgcttcg aatagcagc caagtatcag     600 gtcgaccctg atgcctgctt ttcggccaaa gtgaacaact ctagcctgat tggcttaggg    660
tacactcaga ccctaaaacc aggtatcaaa ctgacgttgt cagccctgct cgatggcaag    720
aacgtcaatg cgggtggcca caagcttggc ctaggactgg aatttcaagc ataa          774
```

<210> SEQ ID NO 5
<211> LENGTH: 257
<212> TYPE: PRT
<213> ORGANISM: Artificial Sequence
<220> FEATURE:
<223> OTHER INFORMATION: SYNTHETIC PEPTIDE

<400> SEQUENCE: 5

```
Ile Lys Leu Asp Leu Lys Thr Lys Ser Glu Asn Gly Leu Glu Phe Thr
1               5                   10                  15

Ser Ser Gly Ser Ala Asn Thr Glu Thr Thr Lys Val Asn Gly Ser Leu
            20                  25                  30

Glu Thr Lys Tyr Arg Trp Thr Glu Tyr Gly Leu Thr Phe Thr Glu Lys
        35                  40                  45

Trp Asn Thr Asp Asn Thr Leu Gly Thr Glu Ile Thr Val Glu Asp Gln
    50                  55                  60

Leu Ala Arg Gly Leu Lys Leu Thr Phe Asp Ser Ser Phe Ser Pro Asn
65                  70                  75                  80

Thr Gly Lys Lys Asn Ala Lys Ile Lys Thr Gly Tyr Lys Arg Glu His
                85                  90                  95

Ile Asn Leu Gly Cys Asp Val Asp Phe Asp Ile Ala Gly Pro Ser Ile
            100                 105                 110

Arg Gly Ala Leu Val Leu Gly Tyr Glu Gly Trp Leu Ala Gly Tyr Gln
        115                 120                 125

Met Asn Phe Glu Thr Ser Lys Ser Arg Val Thr Gln Ser Asn Phe Ala
    130                 135                 140

Val Gly Tyr Lys Thr Asp Glu Phe Gln Leu His Thr Asn Val Asn Asp
145                 150                 155                 160

Gly Thr Glu Phe Gly Gly Ser Ile Tyr Gln Lys Val Asn Lys Lys Leu
                165                 170                 175

Glu Thr Ala Val Asn Leu Ala Trp Thr Ala Gly Asn Ser Asn Thr Arg
            180                 185                 190

Phe Gly Ile Ala Ala Lys Tyr Gln Val Asp Pro Asp Ala Cys Phe Ser
        195                 200                 205

Ala Lys Val Asn Asn Ser Ser Leu Ile Gly Leu Gly Tyr Thr Gln Thr
    210                 215                 220

Leu Lys Pro Gly Ile Lys Leu Thr Leu Ser Ala Leu Leu Asp Gly Lys
225                 230                 235                 240

Asn Val Asn Ala Gly Gly His Lys Leu Gly Leu Gly Leu Glu Phe Gln
                245                 250                 255

Ala
```

<210> SEQ ID NO 6
<211> LENGTH: 774
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC

PEPTIDE

<400> SEQUENCE: 6
ataaaacttg atttgaaaac gaagtccgag aatggattgg aatttactag ctcaggttct      60
gccaacacgg agaccaccaa agtgaacggc agtctggaaa ccaagtacag atggaccgag     120
tatgggctga cgtttactga gaagtggaac acagacaaca ccctgggcac tgagatcacc     180
gtggaagacc agcttgctcg tggactgaag ctgacctttg attcatcttt ctcgcctaac     240
actgggaaaa aaaatgctaa atcaagaca gggtacaaga gggagcatat caacctgggc      300
tgtgatgtgg actttgacat cgctgggccc tcaatccggg cgctctggt gcttggctat      360 gagggttggc tggctggcta ccagatgaat tttgagacct cgaagtcccg agtgacccag     420
agcaactttg cagttggcta caagacggac gaattccagc ttcatactaa tgtgaatgat     480
gggacggagt ttggtggctc catttaccag aaggtgaaca agaagttgga gactgctgtc     540
aatctcgcct ggaccgcagg aaacagtaac actcgctttg gaatagcagc caagtatcag     600
gtcgaccctg atgcctgctt ttcggccaaa gtgaacaact ccagtctaat tggcttaggg     660
tacactcaga ccctaaaacc aggtatcaaa ctgacactgt cagccctgct ggatggcaag     720
aacgtcaatg cgggtggcca caagcttggt ttaggactgg aatttcaagc ataa           774

<210> SEQ ID NO 7
<211> LENGTH: 283
<212> TYPE: PRT
<213> ORGANISM: Homo sapiens

<400> SEQUENCE: 7

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Thr Gly Ser Leu Glu Thr Lys Tyr Arg Trp
    50                  55                  60

Thr Glu Tyr Gly Leu Thr Phe Thr Glu Lys Trp Asn Thr Asp Asn Thr
65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
        115                 120                 125

Met Asp Phe Asp Ile Ala Gly Pro Ser Ile Arg Gly Ala Leu Val Leu
    130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Lys Leu Glu Thr Ala Val Asn Leu
        195                 200                 205

Ala Trp Thr Ala Gly Asn Ser Asn Thr Arg Phe Gly Ile Ala Ala Lys
    210                 215                 220

-continued

```
Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
            245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280

<210> SEQ ID NO 8
<211> LENGTH: 294
<212> TYPE: PRT
<213> ORGANISM: Homo sapiens

<400> SEQUENCE: 8

Met Ala Thr His Gly Gln Thr Cys Ala Arg Pro Met Cys Ile Pro Pro
1               5                   10                  15

Ser Tyr Ala Asp Leu Gly Lys Ala Arg Asp Ile Phe Asn Lys Gly
            20                  25                  30

Phe Gly Phe Gly Leu Val Lys Leu Asp Val Lys Thr Lys Ser Cys Ser
        35                  40                  45

Gly Val Glu Phe Ser Thr Ser Gly Ser Ser Asn Thr Asp Thr Gly Lys
    50                  55                  60

Val Thr Gly Thr Leu Glu Thr Lys Tyr Lys Trp Cys Glu Tyr Gly Leu
65                  70                  75                  80

Thr Phe Thr Glu Lys Trp Asn Thr Asp Asn Thr Leu Gly Thr Glu Ile
                85                  90                  95

Ala Ile Glu Asp Gln Ile Cys Gln Gly Leu Lys Leu Thr Phe Asp Thr
            100                 105                 110

Thr Phe Ser Pro Asn Thr Gly Lys Lys Ser Gly Lys Ile Lys Ser Ser
        115                 120                 125

Tyr Lys Arg Glu Cys Ile Asn Leu Gly Cys Asp Val Asp Phe Asp Phe
    130                 135                 140

Ala Gly Pro Ala Ile His Gly Ser Ala Val Phe Gly Tyr Glu Gly Trp
145                 150                 155                 160

Leu Ala Gly Tyr Gln Met Thr Phe Asp Ser Ala Lys Ser Lys Leu Thr
                165                 170                 175

Arg Asn Asn Phe Ala Val Gly Tyr Arg Thr Gly Asp Phe Gln Leu His
            180                 185                 190

Thr Asn Val Asn Asp Gly Thr Glu Phe Gly Gly Ser Ile Tyr Gln Lys
        195                 200                 205

Val Cys Glu Asp Leu Asp Thr Ser Val Asn Leu Ala Trp Thr Ser Gly
    210                 215                 220

Thr Asn Cys Thr Arg Phe Gly Ile Ala Ala Lys Tyr Gln Leu Asp Pro
225                 230                 235                 240

Thr Ala Ser Ile Ser Ala Lys Val Asn Asn Ser Ser Leu Ile Gly Val
                245                 250                 255

Gly Tyr Thr Gln Thr Leu Arg Pro Gly Val Lys Leu Thr Leu Ser Ala
            260                 265                 270

Leu Val Asp Gly Lys Ser Ile Asn Ala Gly Gly His Lys Val Gly Leu
        275                 280                 285

Ala Leu Glu Leu Glu Ala
    290

<210> SEQ ID NO 9
<211> LENGTH: 283
```

-continued

```
<212> TYPE: PRT
<213> ORGANISM: Homo sapiens

<400> SEQUENCE: 9

Met Cys Asn Thr Pro Thr Tyr Cys Asp Leu Gly Lys Ala Ala Lys Asp
1               5                   10                  15

Val Phe Asn Lys Gly Tyr Gly Phe Gly Met Val Lys Ile Asp Leu Lys
            20                  25                  30

Thr Lys Ser Cys Ser Gly Val Glu Phe Ser Thr Ser Gly His Ala Tyr
        35                  40                  45

Thr Asp Thr Gly Lys Ala Ser Gly Asn Leu Glu Thr Lys Tyr Lys Val
    50                  55                  60

Cys Asn Tyr Gly Leu Thr Phe Thr Gln Lys Trp Asn Thr Asp Asn Thr
65                  70                  75                  80

Leu Gly Thr Glu Ile Ser Trp Glu Asn Lys Leu Ala Glu Gly Leu Lys
                85                  90                  95

Leu Thr Leu Asp Thr Ile Phe Val Pro Asn Thr Gly Lys Lys Ser Gly
            100                 105                 110

Lys Leu Lys Ala Ser Tyr Lys Arg Asp Cys Phe Ser Val Gly Ser Asn
        115                 120                 125

Val Asp Ile Asp Phe Ser Gly Pro Thr Ile Tyr Gly Trp Ala Val Leu
    130                 135                 140

Ala Phe Glu Gly Trp Leu Ala Gly Tyr Gln Met Ser Phe Asp Thr Ala
145                 150                 155                 160

Lys Ser Lys Leu Ser Gln Asn Asn Phe Ala Leu Gly Tyr Lys Ala Ala
                165                 170                 175

Asp Phe Gln Leu His Thr His Val Asn Asp Gly Thr Glu Phe Gly Gly
            180                 185                 190

Ser Ile Tyr Gln Lys Val Asn Glu Lys Ile Glu Thr Ser Ile Asn Leu
        195                 200                 205

Ala Trp Thr Ala Gly Ser Asn Asn Thr Arg Phe Gly Ile Ala Ala Lys
    210                 215                 220

Tyr Met Leu Asp Cys Arg Thr Ser Leu Ser Ala Lys Val Asn Asn Ala
225                 230                 235                 240

Ser Leu Ile Gly Leu Gly Tyr Thr Gln Thr Leu Arg Pro Gly Val Lys
                245                 250                 255

Leu Thr Leu Ser Ala Leu Ile Asp Gly Lys Asn Phe Ser Ala Gly Gly
            260                 265                 270

His Lys Val Gly Leu Gly Phe Glu Leu Glu Ala
        275                 280

<210> SEQ ID NO 10
<211> LENGTH: 283
<212> TYPE: PRT
<213> ORGANISM: Mus musculus

<400> SEQUENCE: 10

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Asn Gly Ser Leu Glu Thr Lys Tyr Arg Trp
    50                  55                  60

Thr Glu Tyr Gly Leu Thr Phe Thr Glu Lys Trp Asn Thr Asp Asn Thr
```

-continued

```
                65                  70                  75                  80
Leu Gly Thr Glu Ile Thr Val Glu Asp Gln Leu Ala Arg Gly Leu Lys
                    85                  90                  95
Leu Thr Phe Asp Ser Ser Phe Ser Pro Asn Thr Gly Lys Lys Asn Ala
                    100                 105                 110
Lys Ile Lys Thr Gly Tyr Lys Arg Glu His Ile Asn Leu Gly Cys Asp
                    115                 120                 125
Val Asp Phe Asp Ile Ala Gly Pro Ser Ile Arg Gly Ala Leu Val Leu
                    130                 135                 140
Gly Tyr Glu Gly Trp Leu Ala Gly Tyr Gln Met Asn Phe Glu Thr Ser
145                 150                 155                 160
Lys Ser Arg Val Thr Gln Ser Asn Phe Ala Val Gly Tyr Lys Thr Asp
                    165                 170                 175
Glu Phe Gln Leu His Thr Asn Val Asn Asp Gly Thr Glu Phe Gly Gly
                    180                 185                 190
Ser Ile Tyr Gln Lys Val Asn Lys Lys Leu Glu Thr Ala Val Asn Leu
                    195                 200                 205
Ala Trp Thr Ala Gly Asn Ser Asn Thr Arg Phe Gly Ile Ala Ala Lys
                    210                 215                 220
Tyr Gln Val Asp Pro Asp Ala Cys Phe Ser Ala Lys Val Asn Asn Ser
225                 230                 235                 240
Ser Leu Ile Gly Leu Gly Tyr Thr Gln Thr Leu Lys Pro Gly Ile Lys
                    245                 250                 255
Leu Thr Leu Ser Ala Leu Leu Asp Gly Lys Asn Val Asn Ala Gly Gly
                    260                 265                 270
His Lys Leu Gly Leu Gly Leu Glu Phe Gln Ala
                    275                 280

<210> SEQ ID NO 11
<211> LENGTH: 295
<212> TYPE: PRT
<213> ORGANISM: Mus musculus

<400> SEQUENCE: 11

Met Ala Glu Cys Cys Val Pro Val Cys Pro Arg Pro Met Cys Ile Pro
1               5                   10                  15
Pro Pro Tyr Ala Asp Leu Gly Lys Ala Ala Arg Asp Ile Phe Asn Lys
                    20                  25                  30
Gly Phe Gly Phe Gly Leu Val Lys Leu Asp Val Lys Thr Lys Ser Cys
                    35                  40                  45
Ser Gly Val Glu Phe Ser Thr Ser Gly Ser Ser Asn Thr Asp Thr Gly
                50                  55                  60
Lys Val Ser Gly Thr Leu Glu Thr Lys Tyr Lys Trp Cys Glu Tyr Gly
65                  70                  75                  80
Leu Thr Phe Thr Glu Lys Trp Asn Thr Asp Asn Thr Leu Gly Thr Glu
                    85                  90                  95
Ile Ala Ile Glu Asp Gln Ile Cys Gln Gly Leu Lys Leu Thr Phe Asp
                    100                 105                 110
Thr Thr Phe Ser Pro Asn Thr Gly Lys Lys Ser Gly Lys Ile Lys Ser
                    115                 120                 125
Ala Tyr Lys Arg Glu Cys Ile Asn Leu Gly Cys Asp Val Asp Phe Asp
                    130                 135                 140
Phe Ala Gly Pro Ala Ile His Gly Ser Ala Val Phe Gly Tyr Glu Gly
145                 150                 155                 160
Trp Leu Ala Gly Tyr Gln Met Thr Phe Asp Ser Ala Lys Ser Lys Leu
```

```
            165                 170                 175
Thr Arg Ser Asn Phe Ala Val Gly Tyr Arg Thr Gly Asp Phe Gln Leu
        180                 185                 190

His Thr Asn Val Asn Asn Gly Thr Glu Phe Gly Gly Ser Ile Tyr Gln
        195                 200                 205

Lys Val Cys Glu Asp Phe Asp Thr Ser Val Asn Leu Ala Trp Thr Ser
        210                 215                 220

Gly Thr Asn Cys Thr Arg Phe Gly Ile Ala Ala Lys Tyr Gln Leu Asp
225                 230                 235                 240

Pro Thr Ala Ser Ile Ser Ala Lys Val Asn Asn Ser Ser Leu Ile Gly
                245                 250                 255

Val Gly Tyr Thr Gln Thr Leu Arg Pro Gly Val Lys Leu Thr Leu Ser
            260                 265                 270

Ala Leu Val Asp Gly Lys Ser Phe Asn Ala Gly His Lys Leu Gly
        275                 280                 285

Leu Ala Leu Glu Leu Glu Ala
        290                 295
```

<210> SEQ ID NO 12
<211> LENGTH: 283
<212> TYPE: PRT
<213> ORGANISM: Mus musculus

<400> SEQUENCE: 12

```
Met Cys Asn Thr Pro Thr Tyr Cys Asp Leu Gly Lys Ala Ala Lys Asp
1               5                   10                  15

Val Phe Asn Lys Gly Tyr Gly Phe Gly Met Val Lys Ile Asp Leu Lys
                20                  25                  30

Thr Lys Ser Cys Ser Gly Val Glu Phe Ser Thr Ser Gly His Ala Tyr
            35                  40                  45

Thr Asp Thr Gly Lys Ala Ser Gly Asn Leu Glu Thr Lys Tyr Lys Val
        50                  55                  60

Cys Asn Tyr Gly Leu Thr Phe Thr Gln Lys Trp Asn Thr Asp Asn Thr
65                  70                  75                  80

Leu Gly Thr Glu Ile Ser Trp Glu Asn Lys Leu Ala Glu Gly Leu Lys
                85                  90                  95

Leu Thr Leu Asp Thr Ile Phe Val Pro Asn Thr Gly Lys Lys Ser Gly
            100                 105                 110

Lys Leu Lys Ala Ser Tyr Arg Arg Asp Cys Phe Ser Leu Gly Ser Asn
        115                 120                 125

Val Asp Ile Asp Phe Ser Gly Pro Thr Ile Tyr Gly Trp Ala Val Leu
    130                 135                 140

Ala Phe Glu Gly Trp Leu Ala Gly Tyr Gln Met Ser Phe Asp Thr Ala
145                 150                 155                 160

Lys Ser Lys Leu Ser Gln Asn Asn Phe Ala Leu Gly Tyr Lys Ala Ala
                165                 170                 175

Asp Phe Gln Leu His Thr His Val Asn Asp Gly Thr Glu Phe Gly Gly
            180                 185                 190

Ser Ile Tyr Gln Lys Val Asn Glu Arg Ile Glu Thr Ser Ile Asn Leu
        195                 200                 205

Ala Trp Thr Ala Gly Ser Asn Asn Thr Arg Phe Gly Ile Ala Ala Lys
    210                 215                 220

Tyr Lys Leu Asp Cys Arg Thr Ser Leu Ser Ala Lys Val Asn Asn Ala
225                 230                 235                 240

Ser Leu Ile Gly Leu Gly Tyr Thr Gln Thr Leu Arg Pro Gly Val Lys
```

```
                    245                 250                 255
Leu Thr Leu Ser Ala Leu Ile Asp Gly Lys Asn Phe Asn Ala Gly Gly
                260                 265                 270

His Lys Val Gly Leu Gly Phe Glu Leu Glu Ala
        275                 280

<210> SEQ ID NO 13
<211> LENGTH: 283
<212> TYPE: PRT
<213> ORGANISM: Rattus norvegicus

<400> SEQUENCE: 13

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Asn Gly Ser Leu Glu Thr Lys Tyr Arg Trp
    50                  55                  60

Thr Glu Tyr Gly Leu Thr Phe Thr Glu Lys Trp Asn Thr Asp Asn Thr
65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
        115                 120                 125

Val Asp Phe Asp Ile Ala Gly Pro Ser Ile Arg Gly Ala Leu Val Leu
    130                 135                 140

Gly Tyr Glu Gly Trp Leu Ala Gly Tyr Gln Met Asn Phe Glu Thr Ser
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Lys Leu Glu Thr Ala Val Asn Leu
        195                 200                 205

Ala Trp Thr Ala Gly Asn Ser Asn Thr Arg Phe Gly Ile Ala Ala Lys
    210                 215                 220

Tyr Gln Val Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280

<210> SEQ ID NO 14
<211> LENGTH: 295
<212> TYPE: PRT
<213> ORGANISM: Rattus norvegicus

<400> SEQUENCE: 14

Met Ala Glu Cys Cys Val Pro Val Cys Gln Arg Pro Ile Cys Ile Pro
1               5                   10                  15
```

Pro Pro Tyr Ala Asp Leu Gly Lys Ala Ala Arg Asp Ile Phe Asn Lys
            20                  25                  30

Gly Phe Gly Phe Gly Leu Val Lys Leu Asp Val Lys Thr Lys Ser Cys
        35                  40                  45

Ser Gly Val Glu Phe Ser Thr Ser Gly Ser Ser Asn Thr Asp Thr Gly
    50                  55                  60

Lys Val Ser Gly Thr Leu Glu Thr Lys Tyr Lys Trp Cys Glu Tyr Gly
65                  70                  75                  80

Leu Thr Phe Thr Glu Lys Trp Asn Thr Asp Asn Thr Leu Gly Thr Glu
                85                  90                  95

Ile Ala Ile Glu Asp Gln Ile Cys Gln Gly Leu Lys Leu Thr Phe Asp
            100                 105                 110

Thr Thr Phe Ser Pro Asn Thr Gly Lys Ser Gly Lys Ile Lys Ser
        115                 120                 125

Ala Tyr Lys Arg Glu Cys Ile Asn Leu Gly Cys Asp Val Asp Phe Asp
        130                 135                 140

Phe Ala Gly Pro Ala Ile His Gly Ser Ala Val Phe Gly Tyr Glu Gly
145                 150                 155                 160

Trp Leu Ala Gly Tyr Gln Met Thr Phe Asp Ser Ala Lys Ser Lys Leu
                165                 170                 175

Thr Arg Ser Asn Phe Ala Val Gly Tyr Arg Thr Gly Asp Phe Gln Leu
            180                 185                 190

His Thr Asn Val Asn Asn Gly Thr Glu Phe Gly Gly Ser Ile Tyr Gln
        195                 200                 205

Lys Val Cys Glu Asp Phe Asp Thr Ser Val Asn Leu Ala Trp Thr Ser
210                 215                 220

Gly Thr Asn Cys Thr Arg Phe Gly Ile Ala Ala Lys Tyr Gln Leu Asp
225                 230                 235                 240

Pro Thr Ala Ser Ile Ser Ala Lys Val Asn Asn Ser Ser Leu Ile Gly
                245                 250                 255

Val Gly Tyr Thr Gln Thr Leu Arg Pro Gly Val Lys Leu Thr Leu Ser
            260                 265                 270

Ala Leu Val Asp Gly Lys Ser Phe Asn Ala Gly His Lys Leu Gly
        275                 280                 285

Leu Ala Leu Glu Leu Glu Ala
    290                 295

<210> SEQ ID NO 15
<211> LENGTH: 283
<212> TYPE: PRT
<213> ORGANISM: Rattus norvegicus

<400> SEQUENCE: 15

Met Cys Ser Thr Pro Thr Tyr Cys Asp Leu Gly Lys Ala Ala Lys Asp
1               5                   10                  15

Val Phe Asn Lys Gly Tyr Gly Phe Gly Met Val Lys Ile Asp Leu Lys
            20                  25                  30

Thr Lys Ser Cys Ser Gly Val Glu Phe Ser Thr Ser Gly His Ala Tyr
        35                  40                  45

Thr Asp Thr Gly Lys Ala Ser Gly Asn Leu Glu Thr Lys Tyr Lys Val
    50                  55                  60

Cys Asn Tyr Gly Leu Ile Phe Thr Gln Lys Trp Asn Thr Asp Asn Thr
65                  70                  75                  80

Leu Gly Thr Glu Ile Ser Trp Glu Asn Lys Leu Ala Glu Gly Leu Lys
                85                  90                  95

```
Leu Thr Val Asp Thr Ile Phe Val Pro Asn Thr Gly Lys Lys Ser Gly
            100                 105                 110
Lys Leu Lys Ala Ser Tyr Arg Arg Asp Cys Phe Ser Val Gly Ser Lys
        115                 120                 125
Val Asp Ile Asp Phe Ser Gly Pro Thr Ile Tyr Gly Trp Ala Val Leu
    130                 135                 140
Ala Phe Glu Gly Trp Leu Ala Gly Tyr Gln Met Ser Phe Asp Thr Ala
145                 150                 155                 160
Lys Ser Lys Leu Cys Gln Asn Asn Phe Ala Leu Gly Tyr Lys Ala Glu
                165                 170                 175
Asp Phe Gln Leu His Thr His Val Asn Asp Gly Thr Glu Phe Gly Gly
            180                 185                 190
Ser Ile Tyr Gln Arg Val Asn Glu Lys Ile Glu Thr Ser Ile Asn Leu
        195                 200                 205
Ala Trp Thr Ala Gly Ser Asn Asn Thr Arg Phe Gly Ile Ala Ala Lys
    210                 215                 220
Tyr Arg Leu Asp Cys Arg Thr Ser Leu Ser Ala Lys Val Asn Asn Ala
225                 230                 235                 240
Ser Leu Ile Gly Leu Gly Tyr Thr Gln Ser Leu Arg Pro Gly Val Lys
                245                 250                 255
Leu Thr Leu Ser Ala Leu Val Asp Gly Lys Asn Phe Asn Ala Gly Gly
            260                 265                 270
His Lys Val Gly Leu Gly Phe Glu Leu Glu Ala
        275                 280

<210> SEQ ID NO 16
<211> LENGTH: 1806
<212> TYPE: DNA
<213> ORGANISM: Homo sapiens

<400> SEQUENCE: 16
gccgctcgct cggctccgct ccctggctcg gctccctgcc tccgcgtcgc agccccgcc      60 gtagccgcct ccgagcccgc cgccacatcc tctgagaaga tggctgtgcc acccacgtat    120
gccgatcttg gcaaatctgc cagggatgtc ttcaccaagg gctatggatt tggcttaata    180
aagcttgatt tgaaaacaaa atctgagaat ggattggaat ttacaagctc aggctcagcc    240
aacactgaga ccaccaaagt gacgggcagt ctggaaacca gtacagatg gactgagtac     300 ggcctgacgt ttacagagaa atggaatacc gacaatacac taggcaccga gattactgtg    360
gaagatcagc ttgcacgtgg actgaagctg accttcgatt catccttctc acctaacact    420
gggaaaaaaa atgctaaaat caagacaggg tacaagcggg agcacattaa cctgggctgc    480
gacatggatt tcgacattgc tgggccttcc atccggggtg ctctggtgct aggttacgag    540
ggctggctgg ccggctacca gatgaatttt gagactgcaa atcccgagt gacccagagc     600 aactttgcag ttggctacaa gactgatgaa ttccagcttc acactaatgt gaatgacggg    660
acagagtttg gcggctccat ttaccagaaa gtgaacaaga gttggagac cgctgtcaat     720 cttgccggga cagcaggaaa cagtaacacg cgcttcggaa tagcagccaa gtatcagatt    780
gaccctgacg cctgcttctc ggctaaagtg aacaactcca gcctgatagg tttaggatac    840
actcagactc taaagccagg tattaaactg acactgtcag ctcttctgga tggcaagaac    900
gtcaatgctg gtggccacaa gcttggtcta ggactggaat tcaagcata aatgaatact     960 gtacaattgt ttaattttaa actattttgc agcatagcta ccttcagaat ttagtgtatc   1020
ttttaatgtt gtatgtctgg gatgcaagta ttgctaaata tgttagccct ccaggttaaa   1080
```

| | |
|---|---|
| gttgattcag ctttaagatg ttacccttcc agaggtacag aagaaaccta tttccaaaaa | 1140 |
| aggtcctttc agtggtagac tcggggagaa cttggtggcc cctttgagat gccaggtttc | 1200 |
| ttttttatct agaaatggct gcaagtggaa gcggataata tgtaggcact ttgtaaattc | 1260 |
| atattgagta aatgaatgaa attgtgattt cctgagaatc gaaccttggt tccctaaccc | 1320 |
| taattgatga gaggctcgct gcttgatggt gtgtacaaac tcacctgaat gggacttttt | 1380 |
| tagacagatc ttcatgacct gttcccaccc cagttcatca tcatctcttt tacaccaaaa | 1440 |
| ggtctgcagg gtgtggtaac tgtttctttt gtgccatttt ggggtggaga aggtggatgt | 1500 |
| gatgaagcca ataattcagg acttattcct tcttgtgttg tgttttttt tggcccttgc | 1560 |
| accagagtat gaaatagctt ccaggagctc cagctataag cttggaagtg tctgtgtgat | 1620 |
| tgtaatcaca tggtgacaac actcagaatc taaattggac ttctgttgta ttctcaccac | 1680 |
| tcaatttgtt ttttagcagt ttaatgggta catttagag tcttccattt tgttggaatt | 1740 |
| agatcctccc cttcaaatgc tgtaattaac aacacttaaa aaacttgaat aaaatattga | 1800 |
| aacctc | 1806 |

<210> SEQ ID NO 17
<211> LENGTH: 1522
<212> TYPE: DNA
<213> ORGANISM: Homo sapiens

<400> SEQUENCE: 17

| | |
|---|---|
| ggttgcggcg gcggaacgg tgtctccttc acttcgccct ccagctgctg cagctgcagc | 60 |
| ccgaccgcga gcgtgccaag cggcttcagc agctagcgga gcggtggcgg cggcccccct | 120 |
| caggacacca ccagattccc ctcttcccgc ggcctcgcca tggcgaccca cggacagact | 180 |
| tgcgcgcgtc caatgtgtat tcctccatca tatgctgacc ttggcaaagc tgccagagat | 240 |
| attttcaaca aaggatttgg ttttggggttg gtgaaactgg atgtgaaaac aaagtcttgc | 300 |
| agtggcgtgg aattttcaac gtccggttca tctaatacag acactggtaa agttactggg | 360 |
| accttggaga ccaaatacaa gtggtgtgag tatggtctga cttttcacaga aaagtggaac | 420 |
| actgataaca ctctgggaac agaaatcgca attgaagacc agatttgtca aggtttgaaa | 480 |
| ctgacatttg atactacctt ctcaccaaac acaggaaaga aaagtggtaa atcaagtct | 540 |
| tcttacaaga gggagtgtat aaaccttggt tgtgatgttg actttgattt tgctggacct | 600 |
| gcaatccatg gttcagctgt ctttggttat gagggctggc ttgctggcta ccagatgacc | 660 |
| tttgacagtg ccaaatcaaa gctgacaagg ataactttg cagtgggcta caggactggg | 720 |
| gacttccagc tacacactaa tgtcaacgat gggacagaat tggaggatc aatttatcag | 780 |
| aaagtttgtg aagatcttga cacttcagta aaccttgctt ggacatcagg taccaactgc | 840 |
| actcgttttg gcattgcagc taaatatcag ttggatccca ctgcttccat ttctgcaaaa | 900 |
| gtcaacaact ctagcttaat tggagtaggc tatactcaga ctctgaggcc tggtgtgaag | 960 |
| cttacactct ctgctctggt agatgggaag agcattaatg ctggaggcca caaggttggg | 1020 |
| ctcgccctgg agttggaggc ttaatccagc tgaaagaaac ctttgggaat ggatatcaga | 1080 |
| agatttggcc ttaatatatt tccattgtga ccagcagcag cttttttcc cccaagaaga | 1140 |
| tgatcaaaac aaaggatgat ctcaacaaga gctgtatttt aagtatttag acagttcttt | 1200 |
| gttagctggt ttctagttgg ttatctagtt accaatgctg cagtcctgca gtcacctata | 1260 |
| cattatttaa atgtatttaa ctgttaaatg cgctacccac caataatgaa atagaccttt | 1320 |
| atgaaaactg tgcaattgtg tgcatgtttg ttttatgtt cctttagaaa acattgactg | 1380 |

| | |
|---|---|
| ttaccattga atgagatgga tcagtggata ttaagatgag gttacaaatt ttgttaagtt | 1440 |
| cagccattat tactttggt atcccagaac atgacaaatt atgaataaaa caagtataca | 1500 |
| taaaaaaaaa aaaaaaaaaa aa | 1522 |

<210> SEQ ID NO 18
<211> LENGTH: 1414
<212> TYPE: DNA
<213> ORGANISM: Homo sapiens

<400> SEQUENCE: 18

| | |
|---|---|
| gggtttgaag accttcagcg ttgccctggc ggacagagac aggccctcgg ggtggaggtc | 60 |
| tttggtttca taagagcctg agagagattt ttctaagata tgtgtaacac accaacgtac | 120 |
| tgtgacctag gaaaggctgc taaggatgtc ttcaacaaag gatatggctt tggcatggtc | 180 |
| aagatagacc tgaaaaccaa gtcttgtagt ggagtggaat tttctacttc tggtcatgct | 240 |
| tacactgata cagggaaagc atcaggcaac ctagaaacca aatataaggt ctgtaactat | 300 |
| ggacttacct tcacccagaa atggaacaca gacaatactc tagggacaga aatctcttgg | 360 |
| gagaataagt tggctgaagg gttgaaactg actcttgata ccatatttgt accgaacaca | 420 |
| ggaaagaaga gtgggaaatt gaaggcctcc tataaacggg attgttttag tgttggcagt | 480 |
| aatgttgata tagattttc tggaccaacc atctatggct gggctgtgtt ggccttcgaa | 540 |
| gggtggcttg ctggctatca tgagtttt gacacagcca aatccaaact gtcacagaat | 600 |
| aatttcgccc tgggttacaa ggctgcggac ttccagctgc acacacatgt gaacgatggc | 660 |
| actgaatttg gaggttctat ctaccagaag gtgaatgaga agattgaaac atccataaac | 720 |
| cttgcttgga cagctgggag taacaacacc cgttttggca ttgctgctaa gtacatgctg | 780 |
| gattgtagaa cttctctctc tgctaaagta aataatgcca gcctgattgg actgggttat | 840 |
| actcagaccc ttcgaccagg agtcaaattg acttatcag ctttaatcga tgggaagaac | 900 |
| ttcagtgcag gaggtcacaa ggttggcttg ggatttgaac tggaagctta atgtggtttg | 960 |
| aggaaagcat cagatttgtc cctggaagtg aagagaaatg aacccactat gttttggcct | 1020 |
| taaaattctt ctgtgaaatt tcaaaagtgt gaactttta ttcttccaaa gaattgtaat | 1080 |
| cctccccaca ctgaagtcta ggggttgcga atccctcctg agggagatgc ttgaaggcat | 1140 |
| gcctggaagt tgtcatgttt gtgccacgtt tcagttcagt tctgaagtgt tattaaatgt | 1200 |
| gttcctcagc gacagtgtag cgtcatgtta gaggagacga tctgacccac cagtttgtac | 1260 |
| atcacgtcct gcatgtccca caccattttt tcatgacctt gtaatatact ggtctctgtg | 1320 |
| ctatagtgga atctttggtt ttgcatcata gtaaaataaa ataaacccat cacatttgga | 1380 |
| acataaaaaa aaaaaaaaaa aaaaaaaaaa aaaa | 1414 |

<210> SEQ ID NO 19
<211> LENGTH: 1767
<212> TYPE: DNA
<213> ORGANISM: Mus musculus

<400> SEQUENCE: 19

| | |
|---|---|
| ccgtagctgc cgctgctccc gccgtcaccg cctccgagaa catggccgtg cctcccacat | 60 |
| acgccgatct tggcaagtcc gccagggatg tcttcaccaa gggctacggc tttggcttaa | 120 |
| taaaacttga tttgaaaacg aagtcagaga atggattgga atttaccagc tcaggctctg | 180 |
| ccaacacgga aaccaccaaa gtgaacggca gcctggaaac caagtacaga tggactgagt | 240 |
| atgggctgac gtttacagag aagtggaaca cagacaacac cctgggcact gagatcactg | 300 |

```
tggaagacca gcttgctcgt ggactgaagc tcacctttga ttcgtcattc tcgccgaaca    360
ctgggaaaaa aaatgctaaa atcaagacag ggtacaagag ggagcacatc aacctcggct    420
gtgacgtgga cttttgacatc gctgggccct cgatccgggg cgctctggtg cttggctatg   480
agggttggct ggctggctac cagatgaatt ttgagacctc gaagtcccga gtgacccaga    540
gcaacttcgc agttggctat aagacggatg aattccagct tcatactaat gtgaatgacg    600
ggacagagtt tggtggctcc atttaccaga aggtgaacaa gaagttggag actgctgtca    660
atctcgcctg gactgcagga acagtaaca ctcgcttcgg aatagcagcc aagtatcagg     720
tcgaccctga tgcctgcttt tcggccaaag tgaacaactc tagcctgatt ggcttagggt    780
acactcagac cctaaaacca ggtatcaaac tgacgttgtc agccctgctc gatggcaaga    840
acgtcaatgc gggtggccac aagcttggcc taggactgga atttcaagca taatgaata    900 ttgtacaatc gtttaatttt aaactatttt gcagcatagc taccttcaga atttagtgta    960 cctttttaatg ttgtatgttg gggatgcgag agttgataaa taccacgtta gacctccagg   1020
ctaaggatga ctcggcttta aggtgtttac catttcagag gtacagcaga accccattc     1080 cagaaagggt cctttttagc tgtaggcgtg ggttggggag gagcccctgt agagatgcca    1140
ggctacaagt ggaaagctgg gaacatgtgg gtcctttgta aatctgtatc cagtccccag    1200
atgaaattgt gacttcccga gcatcgaacc ctggtgtcca gatcctatct gctcggaagc    1260
atgtacacac ctgcgtgaaa gggatgtttt tagactgatc ctcacaccct gttcccatcg    1320
tgccctgttc ccatcctagc ccatcactta acctgtttta caccaaaagt aatctttagg    1380
gtgtggttag ctatttcttt tgtgccattt tagggtggag agggtgggcg tgatggagcc    1440
agtcattcag gaattaattc ttccttgtgt tgtggggtgg ttttctttct cctcctcctc    1500
cttttttttt taattccttc tttcgccatt gcaccagagt atgaaatagc ttccggttct    1560
ccggctctga gctgggcggt gattgtggtc acaccctgac aacactaggg atctcaactg    1620
actccttttg tagcctcacc actatttttt agcagtttaa tgggtacatt atagagtttt    1680
ccattttgtg tggaattagc tcctcccctt caaatgctgt aattaacatc acttaaaata    1740
aaacttgaat aaaatactga aacctcc                                        1767

<210> SEQ ID NO 20
<211> LENGTH: 1662
<212> TYPE: DNA
<213> ORGANISM: Mus musculus

<400> SEQUENCE: 20
ttcacttcgc cctccagccg cggtggctgc agcgcaactt tcagatagcg gagtggcctc     60
agctgcgagc cgagcggtgg cggcagcgcc cctcaggaca cccgcagatc accttttccc   120
cgcgacttcg ccatggctga gtgctgtgta ccggtatgcc cacggccgat gtgtatccct    180
ccaccctatg ctgacctcgg caaagctgcc agagacattt tcaacaaagg atttggcttt    240
gggctggtga agctggatgt gaagacgaag tcatgcagcg gtgtggaatt ttcaacatct    300
ggctcatcta atacagacac tggtaaagtt agcgggacct tggagaccaa gtacaaatgg    360
tgtgagtatg gtctgacttt cacagagaag tggaacaccg ataacactct ggggacagag    420
attgcaattg aagaccagat ttgtcaaggt ttgaaactga cttttgacac cacctttctca   480 ccgaacacag gaaagaaaag tggtaaaatc aagtctgctt acaagaggga gtgtataaac    540
ctcggctgtg atgttgactt tgattttgct ggacctgcca tccatgggtc agctgtcttt    600
ggttacgagg gctggcttgc tgggtaccaa atgacctttg acagtgccaa gtcaaagctg    660
```

-continued

```
acaaggagta actttgcagt cggctacagg actggggact tccagctaca cacaaatgta    720
aataatggga cagaatttgg aggatcaatt tatcagaaag tatgtgaaga ttttgacact    780
tcagtaaacc tcgcttggac atcaggtacc aactgcactc gttttggcat tgcagctaaa    840
taccagttgg atcctactgc ttctatctct gcaaaggtca acaactctag tttaattgga    900
gtgggctata ctcagactct gaggcctggt gtgaagctta cactgtctgc tctggtagac    960
gggaagagct ttaatgctgg aggccacaaa cttgggcttg ccttggaatt ggaggcttaa   1020
tccagttaaa agaaacctct gggaacgaat atcagaagat ttggccttaa tatatttcca   1080
tgcgaccagc aggctcccct tccttccccc agaaggtgat cacatcaaag gatgatgaag   1140
caagagctgt attttaaata tttagacagt cactgttggc tggttcctag ttggatggtt   1200
atcagtgctg ccgtggtgcg gccccctata cattatttaa atgtatttaa ctgttaaatg   1260
tgctacccac caatgatgaa atagacgttt atgaaaaccg tgccatggtg tgcatgtttg   1320
ttttatgttc cttttaacat tgactattgt actgaatgag atggatcagt ggctgtttta   1380
agatgaggta aaagattttt ttttgttata ttcacccatc attagaatta ctttggtaac   1440
cccaaacatg acaaattatg aataaaacaa gtgtacataa ctaatggctc acgtatgtgc   1500
agttacagat tgccagccta gggtctaatc ttcttggcaa atacttttt ctggtgagca    1560 ttttgctctt tacctaaacc tgtgcaacca aattccttgt gtccctagca taatccacga   1620
ggtctttgag attacaataa aatacaagga tacatacttt aa                       1662
```

<210> SEQ ID NO 21
<211> LENGTH: 1345
<212> TYPE: DNA
<213> ORGANISM: Mus musculus

<400> SEQUENCE: 21

```
cgcagacggc gttggttcga gaagaccttc agcgttccct tggtggagcg ggacgggccc     60
accctcgggt tgtagctatg tgtaacacac caacttattg cgacctagga aaggctgcca    120
aggatgtctt taacaaaggg tatgggtttg gcatggtcaa gatagatctg aaaaccaagt    180
cttgtagtgg agtggaattt tctacttcag gtcatgctta tactgataca gggaaagcat    240
caggcaacct agagaccaaa tataaggtct gcaactatgg gctcaccttc acccaaaagt    300
ggaatacaga caatactctt gggacagaaa tctcttggga aataagttg gctgaagggt     360 tgaaactgac tcttgatacc atatttgtac caaacacagg aaagaagagt gggaaattaa    420
aggcctccta tagacgggat tgttttagtc tcggcagtaa tgttgatata gattttttctg    480 gaccgaccat ctatggctgg gctgtgttgg cctttgaagg ttggcttgct ggctatcaga    540
tgagttttga cacagccaaa tccaaactgt ctcagaataa tttcgctctt ggttacaagg    600
ctgcagactt ccagctgcat actcacgtga atgatggcac tgagtttgga ggctcaatct    660
accagaaagt taacgagagg attgaaacgt caataaacct ggcatggaca gctggcagca    720
acaacactcg ttttggcatc gctgctaaat ataagctgga ttgtagaact tctctatctg    780
ccaaagtaaa caatgccagt ttaattggac tgggttatac gcagaccctc cgaccaggag    840
tcaaactgac cctgtcagct ttaatagatg gaaagaactt caatgcagga ggccacaagg    900
ttggattggg atttgaactg gaggcttagt gtggttttga gtagagtatc acttgtccct    960
ggaaatgaag agaaatgaac ccactatgtt ttggccttaa aattctgtga aattcaaaa    1020 gtgtgaactt tttattcttc caagaaattg taattcttcc cacactgaag tctagagatt   1080
acagatctat ccaatgggag gtcctggaag gcatgcctgg aaaattgtcat gtttgtgcca   1140
```

```
catttcagtt gagttctgca gagttaattt aaatatgttc ctcagcaaca acgtagtgtc    1200
atgttaaagg agcgacctgc ctccccggtc tgtacaccgt gtcctgcatg tcccagtcca    1260
cttttccatg gccttttgtt atatcagtct ctgctctagt gagagctttg gttttgcatc    1320
agagtaaaat aaacccatcc tcgtg                                          1345
```

<210> SEQ ID NO 22
<211> LENGTH: 1818
<212> TYPE: DNA
<213> ORGANISM: Rattus norvegicus

<400> SEQUENCE: 22

```
cccagcctcc tcgccgcaac ccccgccgta gctgccgctg ctcccgccgt caccgcctcc     60
gagaacatgg ctgtgcctcc cacatatgct gatcttggca agtccgccag ggatgtcttc    120
accaagggct acggctttgg cttaataaaa cttgatttga aacgaagtc cgagaatgga    180 ttggaattta ctagctcagg ttctgccaac acggagacca ccaaagtgaa cggcagtctg    240
gaaaccaagt acagatggac cgagtatggg ctgacgttta ctgagaagtg aacacagac    300 aacaccctgg gcactgagat caccgtggaa gaccagcttg ctcgtggact gaagctgacc    360
tttgattcat ctttctcgcc taacactggg aaaaaaatg ctaaaatcaa gacagggtac    420
aagagggagc atatcaacct gggctgtgat gtggactttg acatcgctgg ccctcaatc    480 cggggcgctc tggtgcttgg ctatgagggt tggctggctg gctaccagat gaattttgag    540
acctcgaagt cccgagtgac ccagagcaac tttgcagttg gctacaagac ggacgaattc    600
cagcttcata ctaatgtgaa tgatgggacg gagtttggtg gctccattta ccagaaggtg    660
aacaagaagt tggagactgc tgtcaatctc gcctggaccg caggaaacag taacactcgc    720
tttggaatag cagccaagta tcaggtcgac cctgatgcct gcttttcggc caaagtgaac    780
aactccagtc taattggctt agggtacact cagaccctaa aaccaggtat caaactgaca    840
ctgtcagccc tgctggatgg caagaacgtc aatgcgggtg ccacaagct tggtttagga    900 ctggaatttc aagcataaat gaatattgta caatcgttaa ttttaaacta ttttgcagca    960
tagctacctt cagagtttag tgtacctttt aatgtcatat gttggggatg cgagagttga   1020
ttgataccac gttagacctc caggctaagg atgactcggc tttaaggtgt ttaccgtttc   1080
agaggtacag cggaaacccc attccaggaa gggtcctttt tagctgtagg cgtgggctgg   1140
gaggagctcc tctagagatg ccaggctgca agtggaagct gggaacgtgt ggacccttg    1200 taaatctgta tccagttccg cacatgaaat tgtgacttcc tgaacatcga accccggtgt   1260
cccgatcctg tctgctcgga agcatgtaca cacctacgtg aaagggacgg tttttttttt   1320
ttttttatcg gatggtcacg cccggttccc atcgtgccct gttcccatcc tagcccatca   1380
gttacctgtt ttacaccaaa agtagtcttt agggtgtagt tagcaatttc ttttgtgcca   1440
ttttagggtg gagagggtgg gcatgatgaa gccagtcatt caggacttaa ttcttccttg   1500
tgttgtggtg tggttttctt cctttcttct gttttttttt tttaattcc tttttttttt   1560 gccattgcac cagagtatga aatagcttcc aggttgtccg gctcagagct gggcgggtga   1620
ttgtggtcac accctgacaa cactagggat ctcaacggac tcctcttgta gccgcaccac   1680 tattttagc agtttaatgg gtacattata gagtcttcca ttttgtgtgg aattagctcc   1740
tccccttcaa atgctgtaat taacatcact taaaataaaa cttgaataaa atactgaaac   1800
ctcaaaaaaa aaaaaaaa                                                  1818
```

<210> SEQ ID NO 23
<211> LENGTH: 1715
<212> TYPE: DNA
<213> ORGANISM: Rattus norvegicus

<400> SEQUENCE: 23

| | | | | | |
|---|---|---|---|---|---|
| ggggaggcca | ggcttgcggc | ggggcgcaac | ggtgtctcct | tcacttcgcc | ctccagccgc | 60 |
| ggtggctgca | gcgcaacttc | cagatagcgg | agtggcctca | gctgcgagcc | gagcggtggc | 120 |
| ggcagcgccc | ctcaggacac | ccgcagatca | ccttttcccc | gcgacttcgc | catggctgaa | 180 |
| tgttgtgtac | cggtatgcca | acggccaatt | tgtatccctc | caccctatgc | tgaccttggc | 240 |
| aaagctgcca | gagatatttt | caacaaagga | tttggttttg | ggttggtaaa | gctggatgtg | 300 |
| aaaacgaagt | catgcagtgg | tgtggaattt | tcaacatctg | gctcatctaa | tacagacact | 360 |
| ggtaaagtca | gtgggacctt | ggagaccaag | tacaaatggt | gtgagtatgg | tctgactttc | 420 |
| acagagaaat | ggaacactga | caacactctg | gggacggaga | ttgcaattga | agaccagatt | 480 |
| tgtcaaggtt | tgaaactgac | ctttgacacc | acgttttcac | caaacacagg | aaagaaaagt | 540 |
| ggtaaaatca | gtctgcttta | caagagggaa | tgtataaacc | ttggctgtga | tgttgatttt | 600 |
| gattttgctg | gacctgccat | ccatgggtca | gccgtctttg | gttacgaggg | ctggcttgct | 660 |
| gggtaccaga | tgacctttga | cagtgccaag | tcaaagctga | caaggagtaa | cttcgcagtt | 720 |
| ggctacagga | ctggggactt | ccagctacac | acaaatgtaa | ataatgggac | agaatttgga | 780 |
| ggatcaattt | atcagaaagt | atgtgaagat | tttgacactt | cagtaaacct | tgcttggaca | 840 |
| tcaggtacca | actgcactcg | ttttggcatt | gcagctaaat | accagttgga | ccccactgct | 900 |
| tctatttctg | caaaggtcaa | caactctagt | ttaattggag | tgggctatac | tcagactctg | 960 |
| aggcctggtg | tgaagcttac | actgtctgct | ctggtagacg | ggaagagctt | taatgctgga | 1020 |
| ggccacaaac | ttgggcttgc | cttggaattg | gaggcttaat | ccagttaaaa | gaaacctctg | 1080 |
| ggaacggata | tcagaagatt | tggccttaat | atatttccat | gcgaccagca | ggctccccct | 1140 |
| cccccccaga | aggtgatcac | atcaaaggat | gattaagcaa | gagcgtgttt | taaatattta | 1200 |
| gacagtcacc | cgttggctgg | tttctagttg | atggttatc | tcgttatcag | tgctgccgtc | 1260 |
| gtgcggcctc | ctctacatta | tttaatgtac | ttaactgtta | aatgtgctac | ccaccaatga | 1320 |
| tgaaatagac | gttatgaaaa | ccgtgccat | ggtgtgcatg | tttgttttat | gttccttta | 1380 |
| cccttgactc | ttgtactgaa | tgagatggat | cagtggatgt | tttaagatga | ggatgaagat | 1440 |
| cttttttgtg | atattcaccc | atcactagaa | tcactttggt | aaccccaaac | atgacaaatt | 1500 |
| atgaataaaa | cgagtgtaca | caactaatgc | ctcacgtatg | tgcagtcaga | ttgcagccta | 1560 |
| ggggctaatc | ttcttggtaa | atacttctgg | tgagcacttt | gctctttacc | gaaacttggg | 1620 |
| caaccaaact | ccctgtgtcc | ctagcataat | caatccacga | ggtctttgag | actacaataa | 1680 |
| aatacaagga | tacatgcttt | aaaaaaaaaa | aaaaa | | | 1715 |

<210> SEQ ID NO 24
<211> LENGTH: 1380
<212> TYPE: DNA
<213> ORGANISM: Rattus norvegicus

<400> SEQUENCE: 24

| | | | | | |
|---|---|---|---|---|---|
| aggtcgcgca | ggcgcagacg | gcgttggttc | gagaagacct | tcagcgttgc | cttggtggag | 60 |
| cggtacgggc | ccaccctcgg | gttgtagata | tgtgtagcac | accaacttac | tgcgacctag | 120 |
| gaaaggctgc | caaggatgtc | tttaacaaag | ggtatgggtt | tggcatggtc | aaaatagatc | 180 |
| tgaaaaccaa | gtcttgtagt | ggagtggaat | tttctacttc | tggtcatgct | tatactgata | 240 |

```
cagggaaagc atcaggcaac ctagagacca aatataaggt ctgtaactac gggctcatct      300
tcacccaaaa gtggaataca gacaatactc ttgggacaga atctcttgg gagaataagt       360 tggctgaagg gttgaaactg acggttgata ccatatttgt accaaacaca gggaagaaga      420
gtgggaaatt aaaggcctcc tatagacggg attgttttag tgtgggcagt aaggttgaca      480 tagattttc tggaccgacc atctatggct gggccgtgtt ggcctttgaa ggttggcttg       540
ctggctacca gatgagtttt gacacagcca atccaaact gtgtcagaat aattttgctc       600
ttggttacaa ggctgaagac ttccaactgc atactcatgt aaacgatggc actgaatttg     660
gaggctccat ctaccagaga gttaatgaga agatcgaaac atcaataaac ctggcatgga     720
cagctggcag caacaacact cgttttggca tcgctgctaa gtataggctg gattgtagaa     780
cttctctgtc tgccaaagta aacaatgcca gtttaattgg actgggttat acgcagagtc     840
tccgaccggg agtcaaactg accctgtcag ctttagtgga tggaaagaac ttcaatgcag     900
gaggccacaa ggttggcttg ggatttgaac tggaagctta atggggtttt gagtagagta    960
tcaattgtcc ctggaaatga agagaaatga caccactatg ttttggcctt aaaattctgt    1020
gaaatttcaa aagtgaactt tttattcttc caaagaattg taattcttcc cacaccgaag    1080
tctagagatt acagatccat ccagtgggag gtccttgaag gcaatgcctg gaaattgtca    1140
tgtttgtgcc acatttcagt tgagttctgc agagttaatt ttaaatatgt tcctcagcaa    1200
caacgtagtg tcacgttaaa ggaagtgatc tgcccggtct gtacatcgtg tcctgcatgt    1260
cccaactcca ctttccatga cctttgtta catcagtctc tgctctagtg agacctttgg     1320
tttgcatcag agtaaaataa acccatcaca tttggaacat aaaaaaaaaa aaaaaaaaa     1380
```

<210> SEQ ID NO 25
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 25

```
Met Arg Gln Ile Lys Ile Trp Phe Gln Asn Arg Arg Met Lys Trp Lys
1               5                  10                  15

Lys
```

<210> SEQ ID NO 26
<211> LENGTH: 51
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 26

```
atgcgtcaga ttaaaatttg gtttcagaat cgtcgtatga aatggaaaaa a              51
```

<210> SEQ ID NO 27
<211> LENGTH: 32
<212> TYPE: DNA
<213> ORGANISM: Artificial Sequence
<220> FEATURE:
<223> OTHER INFORMATION: Primer

<400> SEQUENCE: 27

```
cgggatccat gataaaactt gatttgaaaa cg                                   32
```

```
<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
gcggccgctt atgcttgaaa ttccagtcc                                29

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
gcggatccat ggccgtgcct                                          20

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
gctctagatt atgcttgaaa ttcc                                     24

<210> SEQ ID NO 31
<211> LENGTH: 25
<212> TYPE: DNA
<213> ORGANISM: Artificial Sequence
<220> FEATURE:
<223> OTHER INFORMATION: Primer

<400> SEQUENCE: 31
gggatgtctt caccaagtgg tacgg                                    25

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
gccgtaccac ttggttgaag acatcc                                   26

<210> SEQ ID NO 33
<211> LENGTH: 283
<212> TYPE: PRT
<213> ORGANISM: Artificial Sequence
<220> FEATURE:
<223> OTHER INFORMATION: SYNTHETIC PEPTIDE

<400> SEQUENCE: 33

Met Ala Val Pro Pro Thr Tyr Ala Asp Leu Gly Lys Ser Ala Arg Asp
1               5                   10                  15

Val Phe Thr Lys Trp Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Thr Gly Ser Leu Glu Thr Lys Tyr Arg Trp
    50                  55                  60
```

```
Thr Glu Tyr Gly Leu Thr Phe Thr Lys Trp Asn Thr Asp Asn Thr
 65                  70                  75                  80

Leu Gly Thr Glu Ile Thr Val Glu Asp Gln Leu Ala Arg Gly Leu Lys
                 85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
        115                 120                 125

Met Asp Phe Asp Ile Ala Gly Pro Ser Ile Arg Gly Ala Leu Val Leu
130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Leu Glu Thr Ala Val Asn Leu
        195                 200                 205

Ala Trp Thr Ala Gly Asn Ser Asn Thr Arg Phe Gly Ile Ala Ala Lys
210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280

<210> SEQ ID NO 34
<211> LENGTH: 26
<212> TYPE: PRT
<213> ORGANISM: Artificial Sequence
<220> FEATURE:
<223> OTHER INFORMATION: SYNTHETIC PEPTIDE

<400> SEQUENCE: 34

Met Ala Val Pro Pro Thr Tyr Ala Asp Leu Gly Lys Ser Ala Arg Asp
1               5                   10                  15

Val Phe Thr Lys Gly Tyr Gly Phe Gly Leu
            20                  25

<210> SEQ ID NO 35
<211> LENGTH: 78
<212> TYPE: DNA
<213> ORGANISM: Artificial Sequence
<220> FEATURE:
<223> OTHER INFORMATION: NUCLEOTIDE SEQUENCE CORRESPONDING TO SYNTHETIC
      PEPTIDE

<400> SEQUENCE: 35
atggctgtgc cacccacgta tgccgatctt ggcaaatctg ccagggatgt cttcaccaag      60
ggctatggat tggctta                                                    78

<210> SEQ ID NO 36
<211> LENGTH: 26
<212> TYPE: PRT
<213> ORGANISM: Artificial Sequence
<220> FEATURE:
```

<223> OTHER INFORMATION: SYNTHETIC PEPTIDE

<400> SEQUENCE: 36

Met Ala Val Pro Pro Thr Tyr Ala Asp Leu Gly Lys Ser Ala Arg Asp
1               5                   10                  15
Val Phe Thr Lys Trp Tyr Gly Phe Gly Leu
            20                  25